United States Patent
Zhang et al.

(10) Patent No.: US 8,574,915 B2
(45) Date of Patent: *Nov. 5, 2013

(54) THYROGLOBULIN QUANTITATION BY MASS SPECTROMETRY

(71) Applicant: Quest Diagnostics Investments Incorporated, Wilmington, DE (US)

(72) Inventors: Yanni Zhang, Mission Viejo, CA (US); Nigel J. Clarke, Oceanside, CA (US); Richard E. Reitz, San Clemente, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/859,551

(22) Filed: Apr. 9, 2013

(65) Prior Publication Data

US 2013/0203099 A1    Aug. 8, 2013

Related U.S. Application Data

(63) Continuation of application No. 13/198,620, filed on Aug. 4, 2011, now Pat. No. 8,455,259, which is a continuation of application No. 12/001,076, filed on Dec. 6, 2007, now Pat. No. 8,030,084.

(51) Int. Cl.
*C12Q 1/00* (2006.01)
*G01N 33/00* (2006.01)

(52) U.S. Cl.
USPC ................ 436/86; 436/171; 436/173; 435/4; 435/7.1

(58) Field of Classification Search
USPC ............................ 43/86, 171, 173; 435/4, 7, 1
See application file for complete search history.

(56) References Cited

U.S. PATENT DOCUMENTS

| | | | |
|---|---|---|---|
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koster |
| 8,030,084 | B2 | 10/2011 | Zhang et al. |
| 2004/0072251 | A1 | 4/2004 | Anderson |
| 2005/0064422 | A1 | 3/2005 | Barnidge et al. |
| 2006/0223188 | A1 | 10/2006 | Soldin |
| 2007/0105179 | A1 | 5/2007 | Madson |
| 2007/0224628 | A1 | 9/2007 | Gordon et al. |
| 2009/0042213 | A1 | 2/2009 | Hoofnagle et al. |

FOREIGN PATENT DOCUMENTS

WO    WO-2008/027861    3/2008

OTHER PUBLICATIONS

Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom, 14:967-73 (2000).

(Continued)

*Primary Examiner* — Krishnan S Menon
*Assistant Examiner* — Rebecca M Fritchman
(74) *Attorney, Agent, or Firm* — Foley & Lardner LLP

(57) ABSTRACT

Provided are methods for determining the amount of thyroglobulin in a sample using various purification steps followed by mass spectrometry. The methods generally involve purifying thyroglobulin in a test sample, digesting thyroglobulin to form peptide T129, purifying peptide T129, ionizing peptide T129, detecting the amount of peptide T129 ion generated, and relating the amount of peptide T129 ion to the amount of thyroglobulin originally present in the sample.

20 Claims, 15 Drawing Sheets

(56) References Cited

OTHER PUBLICATIONS

Bourrell et al., Immunoradiometric Assay of Thyroglobulin in Patients with Differentiated Thyroid Carcinomas: Need for Thyroglobulin Recovery Tests, Clin. Chem. Lab Med, 36(8):725-730 (1998).

Communication pursuant to Article 94(3) EPC dated Jun. 22, 2012 issued in European Patent Application No. 08 860 014.3.

Communication pursuant to Article 94(3) EPC issued in European application No. 08860014.3 dated Nov. 16, 2012.

Di Jeso, et al., Mixed-Disulfide Folding Intermediates between Thyroglobulin and Endoplasmic Reticulum Resident Oxidoreductases ERp57 and protein Disulfide Isomerase, Molecular and Cellular Biology, 25(22):9793-9805 (2005).

Dunn et al., The Sites of Thyroid Hormone Formation in Rabbit Thyroglobulin, The Journal of Biological Chemistry, 262(35):16948-16952 (1987).

Dunn et al., Tyrosine 130 is an Important Outer Ring Donor for Thyroxine Formation in Thyroglobulin, J. Biol. Chem., 273(39):25223-25229 (1998).

Gentile et al. "Identification of hormonogenic tyrosines in fragment 1218-1591 of bovine thyroglobulin by mass spectrometry. Hormonogenic acceptor Tyr-1291 and donor Tyr-1375", Journal of Biological Chemistry, vol. 272, No. 1, 1997, pp. 639-646.

Hoofnagle, et al, "Quantification of Thyroglobulin, a Low-Abundance Serum Protein, by Immunoaffinity Peptide Enrichment and Tandem Mass Spectrometry", Clin Chem, (2008), 54(11):1796-1804.

International Communication issued in European application No. 08860014.3 dated Sep. 20, 2011.

International Preliminary Report on Patentability issued for PCT/US2008/085435 dated Jun. 8, 2010.

International Search Report PCT Application No. PCT/US08/85435 dated Apr. 22, 2009.

Kim et al., Folding and Assembly of Newly Synthesized Thyroblobulin Occurs in a Pre-Golgi Compartment, The Journal of Biological Chemistry, 266(19):12412-12418 (1991).

Merchant, M. and S. R. Weinberger, Recent advancements in surface-enhanced laser desorption/ionization-time of flight-mass spectrometry, Electrophoresis, 21:1164-67, (2000).

Office Action issued for U.S. Appl. No. 12/001,076, dated Apr. 28, 2010.

Persoon et al., Clinical Utility of an Automated Immunochemiluminometric Thyroglobulin Assay in Differentiated Thyroid Carcinoma, Clinical Chem., 52(4):686-691 (2006).

Persoon et al., Thyroblobulin (Tg) Recovery Testing with Quantitative Tg Antibody Measurement for Determining Interference in Serum Tg Assays in Diffferentiated Thyroid Carcinoma, Clinical Chem., 52(6):1196-1199 (2006).

Robb et al., Atmospheric pressure photoionization: An ionization method for liquid chromatography-mass spectrometry, Anal. Chem., 72(15): 3653-3659 (2000).

Salek et al., Analysis of thyroblobulin iodination by tandem mass spectrometry using immonium ions of monoiodo- and diiodo-tyrosine, Proteomics, 5(2):351-353 (2005).

Salm et al., The Quantification of Sirolimus by High-Performance Liquid Chromatography-Tandem Mass Spectrometry and Microparticle Enzyme Immunoassay in Renal Transplant Recipients, Clin. Therapeutics, 22 Supl. B:B71-B85, (2000).

Spencer et al., Detection of Residual and Recurrent Differentiated Thyroid Carcinoma by Serum Thyroglobulin Measurement, Thyroid, 9(5):435-41 (1999).

Spencer et al., Thyroglobulin Measurement Techniques, Clinical Benefits, and Pitfalls, Endocrinol Metab Clin North Am., 24(4):841-863 (1995).

Supplemental European Search Report dated Jan. 28, 2011 in European application No. 08860014.

Taylor et al., Simultaneous Quantification of Tacrolimus and Sirolimus, in Human Blood, by High-Performance Liquid Chromatography-Tandem Mass Spectrometry, Therapeutic Drug Monitoring, 22:608-12, (2000).

US Notice of Allowance issued for U.S. Appl. No. 12/001,076 dated May 11, 2011.

US Notice of Allowance issued for U.S. Appl. No. 13/198,620 dated Dec. 27, 2012.

US Office Action issued for U.S. Appl. No. 13/198,620 dated Nov. 30, 2011.

US Office Action issued for U.S. Appl. No. 13/198,620 dated Sep. 6, 2012.

US Office Action issued for U.S. Appl. No. 12/001,076 dated Jan. 25, 2011.

US Office Action on issued for U.S. Appl. No. 12/001,076 dated Oct. 27, 2010.

Wright et al, Proteinchip surface enhanced laser desorption/ionization (SELDI) mass spectrometry: a novel protein biochip technology for detection of prostate cancer biomarkers in complex protein mixtures, Prostate Cancer and Prostatic Diseases, 2:264-76, (1999).

Figure 1

P01266 Sequence

MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHCVTDCQRNEAGLQCDQNGQYRASQKDRGSGKAFCVDGEGRRLPWWETEAPL
EDSQCLMMQKFEKVPESKVIFDANAPVAVRSKVPDSEFPVMQCLTDCTEDEACSFFTVST
TEPEISCDFYAWTSDNVACMTSDQKRDALGNSKATSFGSLRCQVKVRSHGQDSPAVYLKK
GQGSTTTLQKRFEPTGFQNMLSGLYNPIVFSASGANLTDAHLFCLLACDRDLCCDGFVLT
QVQGGAIICGLLSSPSVLLCNVKDWMDPSEAWANATCPGVTYDQESHQVILRLGDQEFIK
SLTPLEGTQDTFTNFQQVYLWKDSDMGSRPESMGCRKDTVPRPASPTEAGLTTELFSPVD
LNQVIVNGNQSLSSQKHWLFKHLFSAQQANLWCLSRCVQEHSFCQLAEITESASLYFTCT
LYPEAQVCDDIMESNAQGCRLILPQMPKALFRKKVILEDKVKNFYTRLPFQKLMGISIRN
KVPMSEKSISNGFFECERRCDADPCCTGFGFLNVSQLKGGEVTCLTLNSLGIQMCSEENG
GAWRILDCGSPDIEVHTYPFGWYQKPIAQNNAPSFCPLVVLPSLTEKVSLDSWQSLALSS
VVVDPSIRHFDVAHVSTAATSNFSAVRDLCLSECSQHEACLITTLQTQPGAVRCMFYADT
QSCTHSLQGQNCRLLLREEATHIYRKPGISLLSYEASVPSVPISTHGRLLGRSQAIQVGT
SWKQVDQFLGVPYAAPPLAERRFQAPEPLNWTGSWDASKPRASCWQPGTRTSTSPGVSED
CLYLNVFIPQNVAPNASVLVFFHNTMDREESEGWPAIDGSFLAAVGNLIVVTASYRVGVF
GFLSSGSGEVSGNWGLLDQVAALTWVQTHIRGFGGDPRRVSLAADRGGADVASIHLLTAR
ATNSQLFRRAVLMGGSALSPAAVISHERAQQQAIALAKEVSCPMSSSQEVVSCLRQKPAN
VLNDAQTKLLAVSGPFHYWGPVIDGHFLREPPARALKRSLWVEVDLLIGSSQDDGLINRA
KAVKQFEESRGRTSSKTAFYQALQNSLGGEDSDARVEAAATWYYSLEHSTDDYASFSRAL
ENATRDYFIICPIIDMASAWAKRARGNVFMYHAPENYGHGSLELLADVQFALGLPFYPAY
EGQFSLEEKSLSLKIMQYFSHFIRSGNPNYPYEFSRKVPTFATPWPDFVPRAGGENYKEF
SELLPNRQGLKKADCSFWSKYISSLKTSADGAKGGQSAESEEEELTAGSGLREDLLSLQE
PGSKTYSK

Figure 2

P01266-2 Isoform 2 Sequence

```
>sp_vs|P01266-2|THYG_HUMAN Isoform 2 of P01266 - Homo sapiens (Human)
MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHLMQKFEKVPESKVIFDANAPVAVRSKVPDSEFPVMQCLTDCTEDEACSFFT
VSTTEPEISCDFYAWTSDNVACMTSDQKRDALGNSKATSFGSLRCQVKVRSHGQDSPAVY
LKKGQGSTTTLQKRFEPTGFQNMLSGLYNPIVFSASGANLTDAHLFCLLACDRDLCCDGF
VLTQVQGGAIICGLLSSPSVLLCNVKDWMDPSEAWANATCPGVTYDQESHQVILRLGDQE
FIKSLTPLEGTQDTFTNFQQVYLWKDSDMGSRPESMGCRKDTVPRPASPTEAGLTTELFS
PVDLNQVIVNGNQSLSSQKHWLFKHLFSAQQANLWCLSRCVQEHSFCQLAEITESASLYF
TCTLYPEAQVCDDIMESNAQGCRLILPQMPKALFRKKVILEDKVKNFYTRLPFQKLMGIS
IRNKVPMSEKSISNGFFECERRCDADPCCTGFGFLNVSQLKGGEVTCLTLNSLGIQMCSE
ENGGAWRILDCGSPDIEVHTYPFGWYQKPIAQNNAPSFCPLVVLPSLTEKVSLDSWQSLA
LSSVVVDPSIRHFDVAHVSTAATSNFSAVRDLCLSECSQHEACLITTLQTQPGAVRCMFY
ADTQSCTHSLQGQNCRLLLREEATHIYRKPGISLLSYEASVPSVPISTHGRLLGRSQAIQ
VGTSWKQVDQFLGVPYAAPPLAERRFQAPEPLNWTGSWDASKPRASCWQPGTRTSTSPGV
SEDCLYLNVFIPQNVAPNASVLVFFHNTMDREESEGWPAIDGSFLAAVGNLIVVTASYRV
GVFGFLSSGSGEVSGNWGLLDQVAALTWVQTHIRGFGGDPRRVSLAADRGGADVASIHLL
TARATNSQLFRRAVLMGGSALSPAAVISHERAQQQAIALAKEVSCPMSSSQEVVSCLRQK
PANVLNDAQTKLLAVSGPFHYWGPVIDGHFLREPPARALKRSLWVEVDLLIGSSQDDGLI
NRAKAVKQFEESRGRTSSKTAFYQALQNSLGGEDSDARVEAAATWYYSLEHSTDDYASFS
RALENATRDYFIICPIIDMASAWAKRARGNVFMYHAPENYGHGSLELLADVQFALGLPFY
PAYEGQFSLEEKSLSLKIMQYFSHFIRSGNPNYPYEFSRKVPTFATPWPDFVPRAGGENY
KEFSELLPNRQGLKKADCSFWSKYISSLKTSADGAKGGQSAESEEEELTAGSGLREDLLS
LQEPGSKTYSK
```

Figure 3

Q59GF0 (Tg variant-Fragment) Sequence
>Q59GF0|Q59GF0_HUMAN Thyroglobulin variant (Fragment) - Homo sapiens (Human).
IPRKPISKRPVRPSLPRSPRCPLPFNASEVVGGTILCETISGPTGSAMQQCQLLCRQGSW
SVFPPGPLICSLESGRWESQLPQPRACQRPQLWQTIQTQGHFQLQLPPGKMCSADYAGLL
QTFQVFILDELTARGFCQIQVKTFGTLVSIPVCNNSSVQVGCLTRERLGVNVTWKSRLED
IPVASLPDLHDIERALVGKDLLGRFTDLIQSGSFQLHLDSKTFPAETIRFLQGDHFGTSP
RTWFGCSEGFYQVLTSEASQDGLGCVKCPEGSYSQDEECIPCPVGFYQEQAGSLACVPCP
VGRTTISAGAFSQTHCVTDCQRNEAGLQCDQNGQYRASQKDRGSGKAFCVDGEGRRLPWW
ETEAPLEDSQCLMMQKFEKVPESKVIFDANAPVAVRSKVPDSEFPVMQCLTDCTEDEACS
FFTVSTTEPEISCDFYAWTSDNVACMTSDQKRDALGNSKATSFGSLRCQVKVRSHGQDSP
AVYLKKGQGSTTTLQKRFEPTGFQNMLSGLYNPIVFSASGANLTDAHLFCLLACDRDLCC
DGFVLTQVQGGAIICGLLSSPSVLLCNVKDWMDPSEAWANATCPGVTYDQESHQVILRLG
DQEFIKSLTPLEGTQDTFINFQQVYLWKDSDMGSRPESMGCRKNTVPRPASPTEAGLTTE
LFSPVDLNQVIVNGNQSLSSQKHWLFKELFSAQQANLWCLSRCVQEHSFCQLAEITESAS
LYFTCTLYPEAQVCDDIMESNAQGCRLILPQMPKALFRKKVILEDKVKNFYTRLPFQKLT
GISIRNKVPMSEKSISNGFFECERRCDADPCCTGFGFLNVSQLKGGEVTCLTLNSLGIQM
CSEENGGAWRILDCGSPDIEVHTYPFGWYQKPIAQNNAPSFCPLVVLPSLTEKVSLDSWQ
SLALSSVVVDPSIRHFDVAHVSTAATSNFSAVRDLCLSECSQHEACLITTLQTQPGAVRC
MFYADTQSCTHSLQGQNCRLLLREEATEIYRKPGISLLSYEASVPSVPISTHGRLLGRSQ
AIQVGTSWKQVDQFLGVPYAAPPLAERRFQAPEPLNWTGSWDASKPRASCWQPGTRTSTS
PGVSEDCLYLNVFIPQNVAPNASVLVFFHNTMDREESEGWPAIDGSFLAAVGNLIVVTAS
YRVGVFGFLSSGSGEVSGNWGLLDQVAALTWVQTHIRGFGGDPRRVSLAADRGGADVASI
HLLTARATNSQLFRRAVLMGGSALSPAAVISHERAQQQAIALAKEVSCPMSSSQEVVSCL
RQKPANVLNDAQTKLLAVSGPFHYWGPVIDGHFLREPPARALKRSLWVEVDLLIGSSQDD
GLINRAKAVKQFEESQGRISSKTAFYQALQNSLGGEDSDARVEAAATWYYSLEHSTDDYA
SFSRALENATRDYFIICPIIDMASAWAKRARGNVFMYHAPENYGHGSLELLADVQFALGL
PFYPAYEGQFSLEEKSLSLKIMQYFSHFIRSGNPNYPYEFSRKVPTFATPWPDFVPRAGG
ENYKEFSELLPNRQGLKKADCSFWSKYISSLKTSADGAKGGQSAESEEEELTAGSGLRED
LLSLQEPGSKTYSK

Figure 4 (1 of 7)

```
              10         20         30         40         50         60
         MALVLEIFTL LASICWVSAN IFEYQVDAQP LRPCELQRET AFLKQADYVP QCAEDGSFQT
         MALVLEIFTL LASICWVSAN IFEYQVDAQP LRPCELQRET AFLKQADYVP QCAEDGSFQT 70         80         90        100        110        120
         VQCQNDGRSC WCVGANGSEV LGSRQPGRPV ACLSFCQLQK QQILLSGYIN STDTSYLPQC
         VQCQNDGRSC WCVGANGSEV LGSRQPGRPV ACLSFCQLQK QQILLSGYIN STDTSYLPQC 130        140        150        160        170        180
         QDSGDYAPVQ CDVQQVQCWC VDAEGMEVYG TRQLGRPKRC PRSCEIRNRR LLHGVGDKSP
         QDSGDYAPVQ CDVQQVQCWC VDAEGMEVYG TRQLGRPKRC PRSCEIRNRR LLHGVGDKSP 190        200        210        220        230        240
         PQCSAEGEFM PVQCKFVNTT DMMIFDLVHS YNRFPDAFVT FSSFQRRFPE VSGYCHCADS
         PQCSAEGEFM PVQCKFVNTT DMMIFDLVHS YNRFPDAFVT FSSFQRRFPE VSGYCHCADS 250        260        270        280        290        300
         QGRELAETGL ELLLDEIYDT IFAGLDLPST FTETTLYRIL QRRFLAVQSV ISGRFRCPTK
         QGRELAETGL ELLLDEIYDT IFAGLDLPST FTETTLYRIL QRRFLAVQSV ISGRFRCPTK 310        320        330        340        350        360
         CEVERFTATS FGHPYVPSCR RNGDYQAVQC QTEGPCWCVD AQGKEMHGTR QQGEPPSCAE
         CEVERFTATS FGHPYVPSCR RNGDYQAVQC QTEGPCWCVD AQGKEMHGTR QQGEPPSCAE 370        380        390        400        410        420
         GQSCASERQQ ALSRLYFGTS GYFSQHDLFS SPEKRWASPR VARFATSCPP TIKELFVDSG
         GQSCASERQQ ALSRLYFGTS GYFSQHDLFS SPEKRWASPR VARFATSCPP TIKELFVDSG 430        440        450        460        470        480
         LLRPMVEGQS QQFSVSENLL KEAIRAIFPS RGLARLALQF TTNPKRLQQN LFGGKFLVNV
         LLRPMVEGQS QQFSVSENLL KEAIRAIFPS RGLARLALQF TTNPKRLQQN LFGGKFLVNV
```

Figure 4 (2 of 7)

```
              490        500        510        520        530        540
       GQFNLSGALG TRGTFNFSQF FQQLGLASFL NGGRQEDLAK PLSVGLDSNS STGTPEAAKK
       GQFNLSGALG TRGTFNFSQF FQQLGLASFL NGGRQEDLAK PLSVGLDSNS STGTPEAAKK 550        560        570        580        590        600
       DGTMNKPTVG SFGFEINLQE NQNALKFLAS LLELPEFLLF LQHAISVPED VARDLGDVME
       DGTMNKPTVG SFGFEINLQE NQNALKFLAS LLELPEFLLF LQHAISVPED VARDLGDVME 610        620        630        640        650        660
       TVLSSQTCEQ TPERLFVPSC TTEGSYEDVQ CFSGECWCVN SWGKELPGSR VRGGQPRCPT
       TVLSSQTCEQ TPERLFVPSC TTEGSYEDVQ CFSGECWCVN SWGKELPGSR VRGGQPRCPT 670        680        690        700        710        720
       DCEKQRARMQ SLMGSQPAGS TLFVPACTSE GHFLPVQCFN SECYCVDAEG QAIPGTRSAI
       DCEKQRARMQ SLMGSQPAGS TLFVPACTSE GHFLPVQCFN SECYCVDAEG QAIPGTRSAI 730        740        750        760        770        780
       GKPKKCPTPC QLQSEQAFLR TVQALLSNSS MLPTLSDTYI PQCSTDGQWR QVQCNGPPEQ
       GKPKKCPTPC QLQSEQAFLR TVQALLSNSS MLPTLSDTYI PQCSTDGQWR QVQCNGPPEQ 790        800        810        820        830        840
       VFELYQRWEA QNKGQDLTPA KLLVKIMSYR EAASGNFSLF IQSLYEAGQQ DVFPVLSQYP
       VFELYQRWEA QNKGQDLTPA KLLVKIMSYR EAASGNFSLF IQSLYEAGQQ DVFPVLSQYP 850        860        870        880        890        900
       SLQDVPLAAL EGKRPQPREN ILLEPYLFWQ ILNGQLSQYP GSYSDFSTPL AHFDLRNCWC
       SLQDVPLAAL EGKRPQPREN ILLEPYLFWQ ILNGQLSQYP GSYSDFSTPL AHFDLRNCWC 910        920        930        940        950        960
       VDEAGQELEG MRSEPSKLPT CPGSCEEAKL RVLQFIRETE EIVSASNSSR FPLGESFLVA
       VDEAGQELEG MRSEPSKLPT CPGSCEEAKL RVLQFIRETE EIVSASNSSR FPLGESFLVA
```

Figure 4 (3 of 7)

```
            970        980        990       1000       1010       1020
       KGIRLRNEDL GLPPLFPPRE AFAEQFLRGS DYAIRLAAQS TLSFYQRRRF SPDDSAGASA
       KGIRLRNEDL GLPPLFPPRE AFAEQFLRGS DYAIRLAAQS TLSFYQRRRF SPDDSAGASA 1030       1040       1050       1060       1070       1080
       LLRSGPYMPQ CDAFGSWEPV QCHAGTGHCW CVDEKGGFIP GSLTARSLQI PQCPTTCEKS
       LLRSGPYMPQ CDAFGSWEPV QCHAGTGHCW CVDEKGGFIP GSLTARSLQI PQCPTTCEKS 1090       1100       1110       1120       1130       1140
       RTSGLLSSWK QARSQENPSP KDLFVPACLE TGEYARLQAS GAGTWCVDPA SGEELRPGSS
       RTSGLLSSWK QARSQENPSP KDLFVPACLE TGEYARLQAS GAGTWCVDPA SGEELRPGSS 1150       1160       1170       1180       1190       1200
       SSAQCPSLCN VLKSGVLSRR VSPGYVPACR AEDGGFSPVQ CDQAQGSCWC VMDSGEEVPG
       SSAQCPSLCN VLKSGVLSRR VSPGYVPACR AEDGGFSPVQ CDQAQGSCWC VMDSGEEVPG
                                                                   IPRKPI
           1210       1220       1230       1240       1250       1260
       TRVTGGQPAC ESPRCPLPFN ASEVVGGTIL CETISGPTGS AMQQCQLLCR QGSWSVFPPG
       TRVTGGQPAC ESPRCPLPFN ASEVVGGTIL CETISGPTGS AMQQCQLLCR QGSWSVFPPG
       SKRPVRPSLP RSPRCPLPFN ASEVVGGTIL CETISGPTGS AMQQCQLLCR QGSWSVFPPG
           1270       1280       1290       1300       1310       1320
       PLICSLESGR WESQLPQPRA CQRPQLWQTI QTQGHFQLQL PPGKMCSADY ADLLQTFQVF
       PLICSLESGR WESQLPQPRA CQRPQLWQTI QTQGHFQLQL PPGKMCSADY ADLLQTFQVF
       PLICSLESGR WESQLPQPRA CQRPQLWQTI QTQGHFQLQL PPGKMCSADY AGLLQTFQVF
           1330       1340       1350       1360       1370       1380
       ILDELTARGF CQIQVKTFGT LVSIPVCNNS SVQVGCLTRE RLGVNVTWKS RLEDIPVASL
       ILDELTARGF CQIQVKTFGT LVSIPVCNNS SVQVGCLTRE RLGVNVTWKS RLEDIPVASL
       ILDELTARGF CQIQVKTFGT LVSIPVCNNS SVQVGCLTRE RLGVNVTWKS RLEDIPVASL
```

Figure 4 (4 of 7)

```
          1390       1400       1410       1420       1430       1440
    PDLHDIERAL VGKDLLGRFT DLIQSGSFQL HLDSKTFPAE TIRFLQGDHF GTSPRTWFGC
    PDLHDIERAL VGKDLLGRFT DLIQSGSFQL HLDSKTFPAE TIRFLQGDHF GTSPRTWFGC
    PDLHDIERAL VGKDLLGRFT DLIQSGSFQL HLDSKTFPAE TIRFLQGDHF GTSPRTWFGC
          1450       1460       1470       1480       1490       1500
    SEGFYQVLTS EASQDGLGCV KCPEGSYSQD EECIPCPVGF YQEQAGSLAC VPCPVGRTTI
    SEGFYQVLTS EASQDGLGCV KCPEGSYSQD EECIPCPVGF YQEQAGSLAC VPCPVGRTTI
    SEGFYQVLTS EASQDGLGCV KCPEGSYSQD EECIPCPVGF YQEQAGSLAC VPCPVGRTTI
          1510       1520       1530       1540       1550       1560
    SAGAFSQTHC VTDCQRNEAG LQCDQNGQYR ASQKDRGSGK AFCVDGEGRR LPWWETEAPL
    SAGAFSQTHL
    SAGAFSQTHC VTDCQRNEAG LQCDQNGQYR ASQKDRGSGK AFCVDGEGRR LPWWETEAPL
          1570       1580       1590       1600       1610       1620
    EDSQCLMMQK FEKVPESKVI FDANAPVAVR SKVPDSEFPV MQCLTDCTED EACSFFTVST
               MQK FEKVPESKVI FDANAPVAVR SKVPDSEFPV MQCLTDCTED EACSFFTVST
    EDSQCLMMQK FEKVPESKVI FDANAPVAVR SKVPDSEFPV MQCLTDCTED EACSFFTVST
          1630       1640       1650       1660       1670       1680
    TEPEISCDFY AWTSDNVACM TSDQKRDALG NSKATSFGSL RCQVKVRSHG QDSPAVYLKK
    TEPEISCDFY AWTSDNVACM TSDQKRDALG NSKATSFGSL RCQVKVRSHG QDSPAVYLKK
    TEPEISCDFY AWTSDNVACM TSDQKRDALG NSKATSFGSL RCQVKVRSHG QDSPAVYLKK
          1690       1700       1710       1720       1730       1740
    GQGSTTTLQK RFEPTGFQNM LSGLYNPIVF SASGANLTDA HLFCLLACDR DLCCDGFVLT
    GQGSTTTLQK RFEPTGFQNM LSGLYNPIVF SASGANLTDA HLFCLLACDR DLCCDGFVLT
    GQGSTTTLQK RFEPTGFQNM LSGLYNPIVF SASGANLTDA HLFCLLACDR DLCCDGFVLT
          1750       1760       1770       1780       1790       1800
    QVQGGAIICG LLSSPSVLLC NVKDWMDPSE AWANATCPGV TYDQESHQVI LRLGDQEFIK
    QVQGGAIICG LLSSPSVLLC NVKDWMDPSE AWANATCPGV TYDQESHQVI LRLGDQEFIK
    QVQGGAIICG LLSSPSVLLC NVKDWMDPSE AWANATCPGV TYDQESHQVI LRLGDQEFIK
```

Figure 4 (5 of 7)

```
           1810        1820        1830        1840        1850        1860
     SLTPLEGTQD  TFTNFQQVYL  WKDSDMGSRP  ESMGCRKDTV  PRPASPTEAG  LTTELFSPVD
     SLTPLEGTQD  TFTNFQQVYL  WKDSDMGSRP  ESMGCRKDTV  PRPASPTEAG  LTTELFSPVD
     SLTPLEGTQD  TFTNFQQVYL  WKDSDMGSRP  ESMGCRKNTV  PRPASPTEAG  LTTELFSPVD
           1870        1880        1890        1900        1910        1920
     LNQVIVNGNQ  SLSSQKHWLF  KHLFSAQQAN  LWCLSRCVQE  HSFCQLAEIT  ESASLYFTCT
     LNQVIVNGNQ  SLSSQKHWLF  KHLFSAQQAN  LWCLSRCVQE  HSFCQLAEIT  ESASLYFTCT
     LNQVIVNGNQ  SLSSQKHWLF  KHLFSAQQAN  LWCLSRCVQE  HSFCQLAEIT  ESASLYFTCT
           1930        1940        1950        1960        1970        1980
     LYPEAQVCDD  IMESNAQGCR  LILPQMPKAL  FRKKVILEDK  VKNFYTRLPF  QKLMGISIRN
     LYPEAQVCDD  IMESNAQGCR  LILPQMPKAL  FRKKVILEDK  VKNFYTRLPF  QKLMGISIRN
     LYPEAQVCDD  IMESNAQGCR  LILPQMPKAL  FRKKVILEDK  VKNFYTRLPF  QKLTGISIRN
           1990        2000        2010        2020        2030        2040
     KVPMSEKSIS  NGFFECERRC  DADPCCTGFG  FLNVSQLKGG  EVTCLTLNSL  GIQMCSEENG
     KVPMSEKSIS  NGFFECERRC  DADPCCTGFG  FLNVSQLKGG  EVTCLTLNSL  GIQMCSEENG
     KVPMSEKSIS  NGFFECERRC  DADPCCTGFG  FLNVSQLKGG  EVTCLTLNSL  GIQMCSEENG
           2050        2060        2070        2080        2090        2100
     GAWRILDCGS  PDIEVHTYPF  GWYQKPIAQN  NAPSFCPLVV  LPSLTEKVSL  DSWQSLALSS
     GAWRILDCGS  PDIEVHTYPF  GWYQKPIAQN  NAPSFCPLVV  LPSLTEKVSL  DSWQSLALSS
     GAWRILDCGS  PDIEVHTYPF  GWYQKPIAQN  NAPSFCPLVV  LPSLTEKVSL  DSWQSLALSS
           2110        2120        2130        2140        2150        2160
     VVVDPSIRHF  DVAHVSTAAT  SNFSAVRDLC  LSECSQHEAC  LITTLQTQPG  AVRCMFYADT
     VVVDPSIRHF  DVAHVSTAAT  SNFSAVRDLC  LSECSQHEAC  LITTLQTQPG  AVRCMFYADT
     VVVDPSIRHF  DVAHVSTAAT  SNFSAVRDLC  LSECSQHEAC  LITTLQTQPG  AVRCMFYADT
```

Figure 4 (6 of 7)

```
            2170       2180       2190       2200       2210       2220
       QSCTHSLQCQ NCRLLLREEA THIYRKPGIS LLSYEASVPS VPISTHGRLL GRSQAIQVGT
       QSCTHSLQGQ NCRLLLREEA THIYRKPGIS LLSYEASVPS VPISTHGRLL GRSQAIQVGT
       QSCTHSLQGQ NCRLLLREEA THIYRKPGIS LLSYEASVPS VPISTHGRLL GRSQAIQVGT
            2230       2240       2250       2260       2270       2280
       SWKQVDQFLG VPYAAPPLAE RRFQAPEPLN WTGSWDASKP RASCWQPGTR TSTSPGVSED
       SWKQVDQFLG VPYAAPPLAE RRFQAPEPLN WTGSWDASKP RASCWQPGTR TSTSPGVSED
       SWKQVDQFLG VPYAAPPLAE RRFQAPEPLN WTGSWDASKP RASCWQPGTR TSTSPGVSED
            2290       2300       2310       2320       2330       2340
       CLYLNVFIPQ NVAPNASVLV FFHNTMDREE SEGWPAIDGS FLAAVGNLIV VTASYRVGVF
       CLYLNVFIPQ NVAPNASVLV FFHNTMDREE SEGWPAIDGS FLAAVGNLIV VTASYRVGVF
       CLYLNVFIPQ NVAPNASVLV FFHNTMDREE SEGWPAIDGS FLAAVGNLIV VTASYRVGVF
            2350       2360       2370       2380       2390       2400
       GFLSSGSGEV SGNWGLLDQV AALTWVQTHI RGFGGDPRRV SLAADRGGAD VASIHLLTAR
       GFLSSGSGEV SGNWGLLDQV AALTWVQTHI RGFGGDPRRV SLAADRGGAD VASIHLLTAR
       GFLSSGSGEV SGNWGLLDQV AALTWVQTHI RGFGGDPRRV SLAADRGGAD VASIHLLTAR
            2410       2420       2430       2440       2450       2460
       ATNSQLFRRA VLMGGSALSP AAVISHERAQ QQAIALAKEV SCPMSSSQEV VSCLRQKPAN
       ATNSQLFRRA VLMGGSALSP AAVISHERAQ QQAIALAKEV SCPMSSSQEV VSCLRQKPAN
       ATNSQLFRRA VLMGGSALSP AAVISHERAQ QQAIALAKEV SCPMSSSQEV VSCLRQKPAN
            2470       2480       2490       2500       2510       2520
       VLNDAQTKLL AVSGPFHYWG PVIDGHFLRE PPARALKRSL WVEVDLLIGS SQDDGLINRA
       VLNDAQTKLL AVSGPFHYWG PVIDGHFLRE PPARALKRSL WVEVDLLIGS SQDDGLINRA
       VLNDAQTKLL AVSGPFHYWG PVIDGHFLRE PPARALKRSL WVEVDLLIGS SQDDGLINRA
```

Figure 4 (7 of 7)

```
           2530       2540       2550       2560       2570       2580
      KAVKQFEESR GRTSSKTAFY QALQNSLGGE DSDARVEAAA TWYYSLEHST DDYASFSRAL
      KAVKQFEESR GRTSSKTAFY QALQNSLGGE DSDARVEAAA TWYYSLEHST DDYASFSRAL
      KAVKQFEESQ GRTSSKTAFY QALQNSLGGE DSDARVEAAA TWYYSLEHST DDYASFSRAL
           2590       2600       2610       2620       2630       2640
      ENATRDYFII CPIIDMASAW AKRARGNVFM YHAPENYGHG SLELLADVQF ALGLPFYPAY
      ENATRDYFII CPIIDMASAW AKRARGNVFM YHAPENYGHG SLELLADVQF ALGLPFYPAY
      ENATRDYFII CPIIDMASAW AKRARGNVFM YHAPENYGHG SLELLADVQF ALGLPFYPAY
           2650       2660       2670       2680       2690       2700
      EGQFSLEEKS LSLKIMQYFS HFIRSGNPNY PYEFSRKVPT FATPWPDFVP RAGGENYKEF
      EGQFSLEEKS LSLKIMQYFS HFIRSGNPNY PYEFSRKVPT FATPWPDFVP RAGGENYKEF
      EGQFSLEEKS LSLKIMQYFS HFIRSGNPNY PYEFSRKVPT FATPWPDFVP RAGGENYKEF
           2710       2720       2730       2740       2750       2760
      SELLPNRQGL KKADCSFWSK YISSLKTSAD GAKGGQSAES EEEELTAGSG LREDLLSLQE
      SELLPNRQGL KKADCSFWSK YISSLKTSAD GAKGGQSAES EEEELTAGSG LREDLLSLQE
      SELLPNRQGL KKADCSFWSK YISSLKTSAD GAKGGQSAES EEEELTAGSG LREDLLSLQE

PGSKTYSK
      PGSKTYSK
      PGSKTYSK
```

THYROGLOBULIN QUANTITATION BY MASS SPECTROMETRY

CROSS REFERENCE TO RELATED PATENT APPLICATIONS

This application is a Continuation of U.S. application Ser. No. 13/198,620, filed Aug. 4, 2011, which is a Continuation of U.S. application Ser. No. 12/001,076, filed Dec. 6, 2007, now U.S. Pat. No. 8,030,084, the entire contents of each are incorporated by reference herein.

SEQUENCE LISTING

The instant application contains a Sequence Listing which has been submitted in ASCII format via EFS-Web and is hereby incorporated by reference in its entirety. Said ASCII copy, created on Sep. 15, 2011, is named 54769284.txt and is 62,398 bytes in size.

FIELD OF THE INVENTION

The invention relates to the quantitation of thyroglobulin. In a particular aspect, the invention relates to methods for quantitation of thyroglobulin by mass spectrometry.

BACKGROUND OF THE INVENTION

The following description of the background of the invention is provided simply as an aid in understanding the invention and is not admitted to describe or constitute prior art to the invention.

Thyroglobulin, or Tg, is a large dimeric secretary glycoprotein with a molecular weight of 660 kDa comprised of noncovalently bound homodimers.

Tg molecules exist in several forms. The three major Tg molecule sequences as found in the UniProt Knowledgebase (Swiss-Prot+TrEMBL) are P01266 (Human Thyroglobulin Precursor), P01266-2 (Isoform 2 of P01266), and Q59GF02 (Human Thyroglobulin Variant). (See FIGS. 1, 2, and 3, respectively.)

P01266 is the major variant of P01266 with a length of 2768 AA; P01266-2 is an isoform of P01266 with a length of 2711 AA. P01266-2 varies from P01266 at amino acid positions 1510 to 1567 of Tg; and Q59GF0 is a thyroglobulin fragment with a length of 1574 AA. Q59GF0 contains amino acids from positions 1212 to 2768 of Tg.

Tg can only be produced in the thyroid gland and may be produced by either normal well differentiated benign thyroid cells or thyroid cancer cells. It is the precursor protein for thyroid hormone syntheses and serves as the matrix for thyroid iodine storage. Tg is used by the thyroid gland to produce the thyroid hormones thyroxine (T4) and triiodothyroine (T3). Tg levels in the blood can be used as a tumor marker for differentiated thyroid carcinoma (DTC). A high level of Tg in the blood is not by itself an indicator of thyroid cancer, but persistence of Tg in the blood following surgical removal of the thyroid gland indicates persistence of thyroid tissue. A course of treatment following detection of Tg in the blood following surgical removal of the thyroid gland may include administration of radioiodine to ablate all remaining normal thyroid. Continued persistence of Tg in the blood following ablation of all normal thyroid could indicate that some amount of tumor is still present.

Several methods for quantaition of Tg have been developed. For example Spencer, et al., Thyroid, 1999, 9(5):435-41 and Persoon, et al., Clinical Chem 2006, 52(4):686-691 disclose immunometric, radioimmunometric, and immunochemiluminometric methods for quantitation of Tg. These methods are all subject to methodological problems such as differences in standardization, variability in interassay sensitivity and precision, hook effects, and interference attributable to Tg antibodies. The problem of interference attributable to Tg antibodies is particularly troubling for clinical application of monitoring Tg levels as a tumor marker because up to 20% of thyroid cancer patients have Tg autoantibodies.

SUMMARY OF THE INVENTION

The present invention provides methods for quantitation of Tg in a sample by mass spectrometry, including tandem mass spectrometry.

In one aspect, methods are provided for determining the amount of Tg in a test sample that include: (a) subjecting a Tg containing test sample to digestion resulting in creation of Tg peptides; (b) purifying one or more Tg peptides; (c) ionizing one or more Tg peptides; (d) detecting the amount of the Tg peptide ion(s) by mass spectrometry; and (e) relating the amount of detected Tg peptide ion(s) to the amount of Tg in the test sample. A preferred enzyme for preparing Tg peptides is trypsin. A suitable Tg peptide for the method is one that can be evaluated by mass spectrometry and can be sufficiently purified from related peptides that may be generated from proteins other than Tg. An example of one such peptide is peptide T129 (sequence VIFDANAPVAVR) (SEQ ID NO: 4) which contains amino acids from positions 1579 to 1590 of Tg, has a molecular weight of about 1,270 Da, and is present in all three isoforms of Tg. See FIG. 4.

Formation of peptide T129 provides a unique trypsin generated peptide for thyroglobulin. Also, creation of peptide T129 from tryptic digestion of Tg should be unaffected by the presence or absence of the Tg antibodies. Thus, measurement of the increase in peptide T129 in a test sample offers a way of quantitating the amount of Tg originally in the test sample free from inference from Tg antibodies.

Any appropriate method may be used to determine the amount of Tg peptide resulting from digestion of Tg in a sample. In the event that a test sample may contain endogenous Tg peptide, steps may be taken to make certain that the endogenous peptide is not confused with peptide generated by digesting Tg in sample. One approach is to remove the endogenous Tg peptide from the sample before digesting Tg. This may done, for example, using a size separation technique. Another approach is to analyze a portion of a test sample according to the claimed methods but excluding the digestion step in order to establish a baseline level for the endogenous peptide in the test sample. In this approach, the once a baseline is determined, it can be subtracted from the post-digestion level of the peptide, the later representing both the endogenous peptide and that generated by digestion.

Because the methods may be applied to complex test samples (particularly body fluids or test samples derived from tissue), steps may be taken to purify Tg in the test sample prior to digestion. This may done, for example, using a size separation technique.

In some embodiments, the methods include generating one or more Tg peptide ions in which at least one of the ions has a mass/charge ratio (m/z) corresponding to that of (singly or multiply charged) peptide T129 ions. In preferred related embodiments, the methods include generating one or more Tg peptide ions in which at least one has m/z of 1272.8±0.5, 636.4±0.5, or 424.3±0.5 (corresponding to singly, doubly, or triply charged peptide T129 ions). In related preferred embodiments, the methods may include generating one or more fragment ions of a Tg peptide ion in which at least one has a m/z of 541.3±0.5, 612.3±0.5, 726.4±0.5, 797.4±0.5, 912.4±0.5, or 1059.5±0.5; preferably one or more of the fragment ions are selected from the group consisting of ions with a m/z of 797.4±0.5, 912.4±0.5, and 1059.5±0.5.

In some embodiments, the purification in step (b) is accomplished with at least one size separation technique. Preferably, size separation techniques may be filtration, LC, or any combination thereof. In certain preferred embodiments, the test sample is a body fluid or tissue. In some embodiments, an additional step is included where a second quantity of the test sample is subjected to steps (b) through (e) in order to establish a baseline level of one or more endogenous Tg peptides. In these embodiments, this baseline level can be subtracted from the amount of Tg peptide ion(s) detected in the test sample to determine the amount of Tg peptide ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weigh cut off that allows for retention of Tg above the filter and allows Tg peptides to pass through with the filtrate. In related embodiments, the molecular weigh cut-off is about 2 kD to 300 kD; more preferably about 100 kD to 300 kD. In these embodiments, the two filtrations (pre-digestion and step (b)) may be conducted with the same filter.

In a second aspect, methods are provided for determining the amount of Tg in a test sample that include: (a) subjecting a Tg containing test sample to digestion resulting in creation of peptide T129; (b) purifying peptide T129; (c) ionizing peptide T129 to generate a precursor ion with a m/z of 636.4±0.5; (d) fragmenting the peptide T129 precursor ion to form one or more fragment ions in which at least one has a m/z of about 797.4±0.5, 912.4±0.5, or 1059.5±0.5; detecting the amount of peptide T129 precursor ions, one or more fragment ions, or both, by mass spectrometry; and (e) relating the amount of detected ion(s) to the amount of Tg in the test sample. In certain preferred embodiments, the test sample is a body fluid or tissue or tissue. In some embodiments, an additional step is included where a second quantity of the test sample is subjected to steps (b) through (e) in order to establish a baseline level of one or more endogenous peptide T129. In these embodiments, this baseline level can be subtracted from the amount of peptide T129 ion(s) detected in the test sample to determine the amount of peptide T129 ion(s) that result from Tg in the original test sample. In other embodiments, the methods include an additional initial step of purifying Tg in the test sample prior to digestion. In these embodiments, the pre-digestion purification and/or the purification in step (b) may each be accomplished with at least one size separation technique. Preferably, at least one size separation technique used in both pre-digestion purification and step (b) is filtration; more preferably, this filtration is done with a molecular weight cut-off filter with molecular weigh cut off that allows for retention of Tg above the filter and allows Tg peptides to pass through with the filtrate. In related embodiments, the molecular weigh cut-off is about 2 kD to 300 kD; more preferably about 100 kD to 300 kD. In these embodiments, the two filtrations (pre-digestion and step (b)) may be conducted with the same filter.

As used herein, the term "purification" or "purifying" does not refer to removing all materials from the sample other than the analyte(s) of interest. Instead, purification refers to a procedure that enriches the amount of one or more analytes of interest relative to one or more other components of the sample. Purification, as used herein, does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

As used herein, the term "about" in reference to quantitative measurements, not including the measurement of mass of an ion, refers to the indicated value plus or minus 10%.

As used herein, the term "substantially all" refers to any proportion greater than 50%, more preferably greater than 60%, more preferably greater than 70%, more preferably greater than 80%, and more preferably greater than 90%.

As used herein, the term "test sample" refers to any sample that may contain Tg. As used herein, the term "body fluid or tissue" means any fluid or tissue that can be isolated from the body of an individual. For example, "body fluid or tissue" may include blood, plasma, serum, bile, saliva, urine, tears, perspiration, and the like. If solid tissue is to be analyzed, it may be processed to release a liquid fraction that could contain any Tg present in the tissue. The liquid fraction can then be subject to the methods described herein.

As used herein, the term "digestion" means proteolytic cleavage of proteins into peptides. Digestion agents may include trypsin, Lyc-C, Arg-R, Asp-N and the like. Digestion is carried out by adding a digestion agent (i.e., an enzyme) to a sample and incubating for some period of time.

As used herein, "Tg" or "Tg molecule" means an intact Tg protein molecule.

As used herein, the term "Tg peptide" means any peptide of 100 amino acids or less that is a fragment of the native Tg. Tg peptides can be endogenous to a test sample or formed as a result of digestion of Tg. Peptide T129 is an example of a Tg peptide formed as a result of trypsin digestion of Tg.

As used herein, the term "size separation technique" means any technique (physical or chemical) that allows for the separation of at least one species from a test sample based on any one or more of molecular weight and shape. Examples of such techniques include, but are not limited to, filtration, chromatography, and certain aspects of mass spectrometry.

As used herein, the term "chromatography" refers to a process in which a chemical mixture carried by a liquid or gas is separated into components as a result of differential distribution of the chemical entities as they flow around, over, and/or through a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "high performance liquid chromatography" or "HPLC" refers to liquid chromatography in which the degree of separation is increased by forcing the mobile phase under pressure through a stationary phase, typically a densely packed column.

As used herein, the term "mass spectrometry" or "MS" refers to an analytical technique to identify compounds by their mass. MS refers to methods of filtering, detecting, and measuring ions based on their m/z. MS technology generally includes (1) ionizing the compounds to form charged species (e.g., ions); and (2) detecting the molecular weight of the ions and calculating their m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

As used herein, the term "operating in positive ion mode" refers to those mass spectrometry methods where positive ions are detected. Similarly, the term "operating in negative ion mode" refers to those mass spectrometry methods where negative ions are detected.

As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectrometry where the mechanism for the photoionization of molecule M is photon absorption and electron ejection to form the molecular M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. Robb, D. B., Covey, T. R. and Bruins, A. P. (2000): See, e.g., Robb et al., Atmospheric pressure photoionization: An ionization method for liquid chromatography-mass spectrometry. *Anal. Chem.* 72(15): 3653-3659.

As used herein, the term "inductively coupled plasma" or "ICP" refers to methods in which a sample is interacted with a partially ionized gas at a sufficiently high temperature to atomize and ionize most elements As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

As used herein, the term "limit of quantification" or "LOQ" refers to the point where measurements become quantitatively meaningful. The analyte response at this LOQ is identifiable, discrete and reproducible with a precision of 20% and an accuracy of 80% to 120%.

In certain preferred embodiments of the methods disclosed herein, mass spectrometry is performed in positive ion mode. In certain particularly preferred embodiments of the methods disclosed herein, mass spectrometry is performed using ESI as the method of creating ions from Tg peptides.

In preferred embodiments, the ions from Tg peptide ionization detectable in a mass spectrometer are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of about 636.4±0.5, and the fragment ions have a m/z of 1059.5±0.5, 921.4±0.5, or 797.4±0.5.

In some preferred embodiments, a separately detectable internal standard peptide (e.g., T129) is introduced in the test sample after trypsin digestion. In these embodiments, all or a portion of the peptide present in the test sample both from digestion of endogenous Tg and the addition of the internal standard are ionized to produce a plurality of ions detectable in a mass spectrometer, and one or more ions produced from the peptide ionization are detected in a mass spectrometer.

In other preferred embodiments, a separately detectable internal Tg standard is provided in the test sample prior to trypsin digestion. In these embodiments, all or a portion of both the endogenous Tg and the internal standard present in the test sample are digested by trypsin resulting in formation of Tg peptides. Tg peptides are ionized to produce a plurality of ions detectable in a mass spectrometer, and one or more ions produced from Tg peptide ionization are detected by mass spectrometry.

In preferred embodiments, the ions detectable in a mass spectrometer produced from the ionization of Tg peptides resulting from Tg digestion are selected from the group consisting of ions with a m/z of 636.4±0.5, 1059.5±0.5, 921.4±0.5, 797.4±0.5, 726.4±0.5, 612.3±0.5, and 541.3±0.5; the first ion listed (m/z of 636.4±0.5) being a precursor ion with a net charge of positive 2 electron units and the latter six ions listed being fragment ions of the precursor ion. In particularly preferred embodiments, the precursor ion has a net charge of positive 2 electron units and a m/z of 636.4±0.5, and the fragment ions have a m/z of 1059.5±0.5, 921.4±0.5, 797.4±0.5.

In preferred embodiments, the presence or amount of Tg peptide ions is related to the presence or amount of Tg in the original test sample by comparison to a reference Tg sample.

In one embodiment, the methods involve the combination of LC with mass spectrometry. In another preferred embodiment, the mass spectrometry is tandem mass spectrometry (MS/MS).

The summary of the invention described above is non-limiting and other features and advantages of the invention will be apparent from the following detailed description of the invention, and from the claims.

BRIEF DESCRIPTION OF THE DRAWINGS

FIG. 1 shows the amino acid sequence for P01266 (Human Thyroglobulin Precursor) (SEQ ID NO: 1).

FIG. 2 shows the amino acid sequence for P01266-2 (Isoform 2 of P01266) (SEQ ID NO: 2).

FIG. 3 shows the amino acid sequence for Q59GF0 (Thyroglobulin Variant-Fragment) (SEQ ID NO: 3).

FIG. 4 shows a comparison of the three sequences contained in FIGS. 1-3 demonstrating that they all contain amino acids corresponding to positions 1579 to 1590 of Tg. Sequence P01266 is on top (SEQ ID NO: 1); sequence P01266-2 is in the middle (SEQ ID NO: 2); and sequence Q59GF0 is at the bottom (SEQ ID NO: 3).

DETAILED DESCRIPTION OF THE INVENTION

Figure 5:
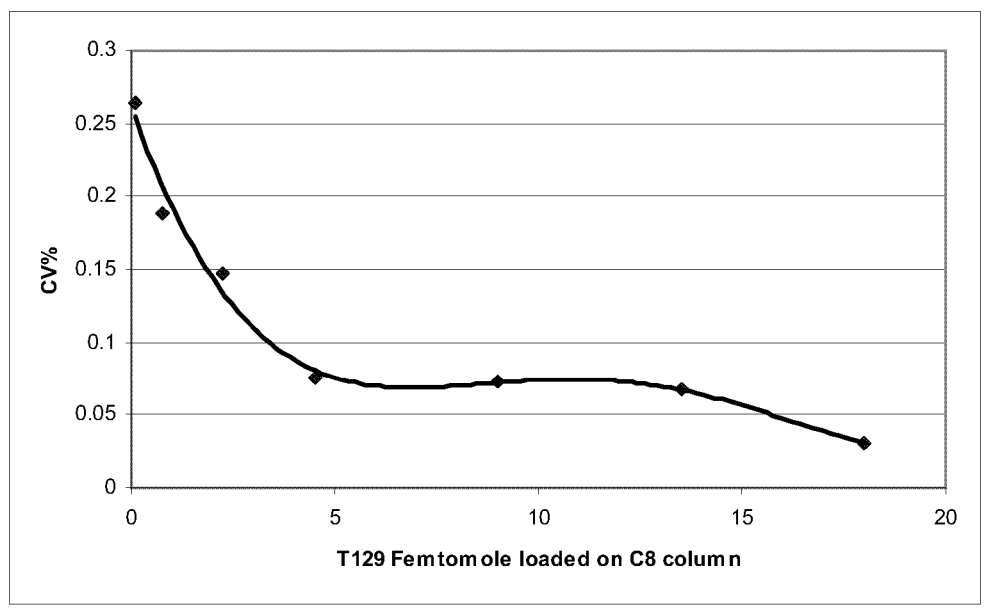
FIG. 5 shows the limit of quantitation verification for Tg peptide ion with m/z corresponding to peptide T129 by MS/MS. The equation describing the trend line for FIG. 5 is as follows: $y = 1E-05x^4 - 0.0007x^3 + 0.0114x^2 - 0.0787x + 0.2606$. $R^2 = 0.9833$ for this fit. Details are described in Example 1.

Methods are described for quantitatively measuring Tg in a test sample. This quantitative measurement is achieved through the use of LC-MS/MS techniques. Prior to the use of LC-MS/MS, samples may be prepared by the following technique, or any portion thereof. A first purification of Tg in a test sample may be conducted through the use of a size separation technique such that substantially all Tg in the test sample is retained. Following the first purification step, enzymatic digestion of Tg may be carried out creating Tg peptides of interest. After digestion, another utilization of a size separation technique may be employed such that a selected Tg peptide generated in the enzymatic digestion of Tg is purified. This second size separation technique can be used to remove substantially all undigested, higher-molecular weight species. Properly executed, the sample preparation techniques ensure that selected Tg peptides quantitated by LC-MS/MS directly result from enzymatic digestion of Tg originally in the test sample; thus, the level of selected Tg peptides in the test sample at the start of LC-MS/MS is directly proportional to the amount of Tg originally present in the test sample.

Any suitable size separation technique may be utilized, but in the examples that follow, both the first and second size separation techniques are filtration through a molecular weight cut-off filter. It is also possible, as discussed in the Examples that follow, to select a molecular weight cut-off filter with an appropriate molecular weight cut-off such that the same filter can be used for both the first size separation and the second size separation.

LC, most preferably HPLC, is utilized, may be utilized either alone or in combination with other purification methods, to purify selected Tg peptides. This purification is combined with MS/MS, thereby providing an assay system for quantifying selected Tg peptides in a test sample. The quantity of the selected Tg peptides in the test sample is then used to determine the quantity of Tg in the original test sample. The Tg quantitation methods provided herein have enhanced specificity and are less subject to methodological problems (such as Tg antibody interference).

Suitable test samples may include any test sample that may contain the analyte of interest. In some preferred embodiments, a sample is a biological sample; that is, a sample obtained from any biological source, such as an animal, a cell culture, an organ culture, and the like. In certain preferred embodiments, samples are obtained from a mammalian animal, such as a dog, cat, horse, etc. Particularly preferred mammalian animals are primates, most preferably humans. Particularly preferred samples include blood, plasma, serum, urine, saliva, tears, cerebrospinal fluid, or other body fluid or tissue samples. Such samples may be obtained, for example, from a patient; that is, a living person presenting oneself in a clinical setting for diagnosis, prognosis, or treatment of a disease or condition. The test sample is preferably obtained from a patient, for example, serum or plasma.

Sample Preparation for Mass Spectrometry

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, centrifugation, combinations thereof and the like. In certain preferred embodiments, Tg present in a test sample prior to enzymatic digestion.

Filtration is one preferred method of preparing a test sample, especially a biological test sample, such as serum or plasma, for chromatography. Such filtration is carried out by filtering a test sample through a molecular weight cut-off filter to separate species with molecular weights higher than the filter's cut-off (including Tg) from those with molecular weights lower than the filter's cut-off. The test sample remaining above the filter following complete (or near complete) filtration is substantially free of potentially interfering species with molecular weights lower than the filter's cut-off.

The pH of the test sample may then be adjusted to any point required by a digestion agent. In certain preferred embodiments, the digestion agent is trypsin and pH can be adjusted with a solution of ammonium acetate to have a pH suitable for this enzyme. In these preferred embodiments, the sample is then digested with trypsin to form Tg peptides (including peptide T129).

After trypsin digestion, the sample may be purified with a second filtration. This post-digestion filtration can be carried out similarly to the pre-digestion filtration described above (with the exception that the filtrate is retained), in order to separate Tg fragments from potentially interfering species with molecular weights higher than the filter's cut-off that may also be present in the sample. The filtrate from this post-digestion filtration can then be purified by liquid chromatography and subsequently subjected to mass spectrometry analysis.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art may select HPLC instruments and columns that are suitable for use in the methods. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-8 bonded groups. The chromatographic column includes an inlet port for receiving a sample and an outlet port for discharging an effluent that includes the fractionated sample.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one embodiment, the sample to be analyzed is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e. mixed) mode. In preferred embodiments, HPLC is performed on an analytical HPLC system with a C8 solid phase using 0.2% formic acid in HPLC Grade Ultra Pure Water and 0.2% formic acid in 100% methanol as the mobile phases.

Numerous column packings are available for chromatographic separation of samples and selection of an appropriate separation protocol is an empirical process that depends on the sample characteristics, analyte of interest, presence of interfering substances and their characteristics, etc. Commercially available HPLC columns include, but are not limited to, polar, ion exchange (both cation and anion), hydrophobic interaction, phenyl, C-2, C-8, C-18, and polar coating on porous polymer columns.

In one embodiment, the HPLC column has a C8 solid phase with a median particle size of 5 μm (nominal) and a median particle pore size of 100 Å. In a preferred embodiment the column dimensions are 1.0 mm ID×50 mm length (Phenomenex Corp. Luna 5μ C8(2) 100 Å New Column 50×1.0 mm, Phenomenex Cat. No. 00B-4249-A0 or equivalent).

During chromatography, the separation of materials is effected by variables such as choice of eluent (also known as a "mobile phase"), choice of gradient elution and the gradient conditions, temperature, etc.

Detection and Quantitation by Mass Spectrometry

In various embodiments, Tg peptides may be ionized by any method known to the skilled artisan. Mass spectrometry is performed using a mass spectrometer, which includes an ion source for ionizing the fractionated sample and creating charged molecules for further analysis. Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In preferred embodiments, Tg peptides are ionized by electrospray ionization (ESI) creating Tg peptide precursor ions. In related preferred embodiments, Tg peptide precursor ions are in a gaseous state and the inert collision gas is argon.

After the sample has been ionized, the positively charged ions thereby created may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). In preferred embodiments, ions are detected using SRM.

Preferably, m/z is determined using a quadrupole instrument. In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps may be combined in methods known as "MS/MS". Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 400 to 1600 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of Tg. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the LC purification and mass spectrometry steps may be performed in an on-line fashion.

In certain embodiments, techniques such as MS/MS are used to isolate precursor ions for further fragmentation. In these embodiments, collision activation dissociation (CAD) may be used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy. In alternative embodiments, electron transfer dissociation (ETD) may be used to generate the fragment ions. In ETD, radical anions are used to transfer electrons to multiply charged peptide or protein cations resulting in random cleavage along the peptide backbone.

In particularly preferred embodiments, Tg is detected and/or quantified using LC-MS/MS as follows. A Tg peptide enriched test sample prepared as described above is subjected to LC. The flow of liquid solvent from the chromatographic column enters the heated nebulizer interface of a LC-MS/MS analyzer and the solvent/analyte mixture is converted to vapor in the heated tubing of the interface. The analyte (e.g., Tg peptides), contained in the nebulized solvent, is ionized by the corona discharge needle of the interface, which applies a large voltage to the nebulized solvent/analyte mixture. The ions (i.e. Tg peptide precursor ions) pass through the orifice of the instrument and enter the first quadrupole. Quadrupoles 1 and 3 (Q1 and Q3) are mass filters, allowing selection of ions (i.e., "precursor" and "fragment" ions) based on their m/z. Quadrupole 2 (Q2) is the collision cell, where ions are fragmented. Q1 selects for ions with m/z of peptide T129 precursor ions (m/z of 636.4±0.5). Selected precursor ions are allowed to pass into the collision chamber (Q2), while ions with any other m/z collide with the sides of Q1 and are eliminated. Precursor ions entering Q2 may be fragmented with collision activated dissociation (CAD) through collisions with neutral argon gas molecules. Alternatively, if the precursor ions entering Q2 are multiply charged cations, they may be fragmented with electron transfer dissociation (ETD). The fragment ions generated are passed into Q3, where selected fragment ions are collected while other ions are eliminated.

Using standard methods well known in the art, one of ordinary skill is capable of identifying one or more fragment ions of a particular Tg peptide precursor ion that may be used for selection in Q3. A specific fragment ion is one that will not be formed in significant amounts by other molecules with similar molecular structures. In contrast, a non-specific fragment ion is one that is formed by molecules other than the desired analyte. Suitable specific fragment ions can be identified by testing various molecular standards to determine whether fragment ions formed by a selected Tg peptide are also formed by other molecules with similar structures or features. Preferably, at least one fragment ion specific for Tg peptide ions with m/z corresponding to that of peptide T129 ions are identified. More preferably, one or more of these fragment ions have m/z of 797.4±0.5, 912.4±0.5 or 1059.5±0.5.

As ions collide with the detector they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of Tg peptides with m/z corresponding to peptide T129. As described above, the relative abundance of a given ion may be converted into an absolute amount of the original analyte using calibration standard curves based on peaks of one or more ions of an internal molecular standard. The absolute amount of an analyte detected by LC-MS/MS can then be converted into an absolute amount of Tg that was present in the original test sample.

The following examples serve to illustrate the invention. These examples are in no way intended to limit the scope of the methods.

EXAMPLES

Example 1

Demonstration of MS Quantitation of Peptide T129

Several samples with various known concentrations of peptide T129 were prepared by series dilution starting with a sample of known peptide T129 concentration. Peptide T129 LOQ and calibration curves were developed from LC-MS/MS analysis of these samples.

LC was performed with a Phenomenex analytical column (Phenomenex Corp. Luna 5μ C8(2) 100 Å New Column 50×1.0 mm). A binary HPLC eluent composed of 0.2% formic acid in ultra pure water (HPLC grade) (mobile phase A) and 0.2% formic acid in 100% methanol (mobile phase B) was applied to the analytical column to separate selected Tg peptides from other species contained in the sample. The binary eluent was applied according to the following gradient profile: as a first step, an 80/20 mixture of mobile phase A/mobile phase B was applied for 120 seconds; as a second step, a 30/70 mixture of mobile phase A/mobile phase B was applied for 60 seconds; as a third step, the relative amount of mobile phase B in the mixture was ramped to a 5/95 mixture of mobile phase A/mobile phase B over a period of 120 seconds; as a fourth step, a 5/95 mixture of mobile phase A/mobile phase B was applied for 60 seconds; as a fifth and final step, an 80/20 mixture of mobile phase A/mobile phase B was applied for 240 seconds.

The separated sample was then subjected to MS/MS for quantitation of one or more Tg peptides with m/z corresponding to peptide T129.

MS/MS was performed using a Finnigan TSQ Quantum Ultra MS/MS system (Thermo Electron Corporation). The following software programs all from ThermoElectron were used in the Examples described herein: Tune Master V1.2 or newer, Xcalibur V 2.0 SR1 or newer, TSQ Quantum 1.4 or newer, LCQuan V 2.0 or newer, and XReport 1.0 or newer.

Liquid solvent/analyte exiting the analytical HPLC column flowed to the heated nebulizer interface of a Thermo Finnigan MS/MS analyzer. The solvent/analyte mixture was converted to vapor in the heated tubing of the interface. Analytes in the nebulized solvent were ionized by the corona discharge needle of the interface, which applied voltage to the nebulized solvent/analyte mixture.

Ions passed to the first quadrupole (Q1), which selected ions with a m/z of 636.4±0.5. Ions entering Quadrupole 2 (Q2) collided with argon gas to generate ion fragments, which were passed to quadrupole 3 (Q3) for further selection. Mass transitions used for quantitation of precursor ions with m/z corresponding to peptide T129 during validation on positive polarity are shown in Table 1.

TABLE 1

Mass transitions for precursor ions with m/z corresponding to peptide T129 (Positive Polarity)

| Precursor Ion (m/z) | Fragment Ion (m/z) |
|---|---|
| 636.4 ± 0.5 | 797.4 ± 0.5, 912.4 ± 0.5 & 1059.5 ± 0.5 |

To determine the limit of quantitation (LOQ) with a precision of 20% and an accuracy of 80% to 120%, seven different samples at varying concentrations were assayed and the reproducibility (CV) determined for each. The LOQ for one or more Tg peptides with m/z corresponding to peptide T129 was defined at about 67 amol/μl.

Figure 6:
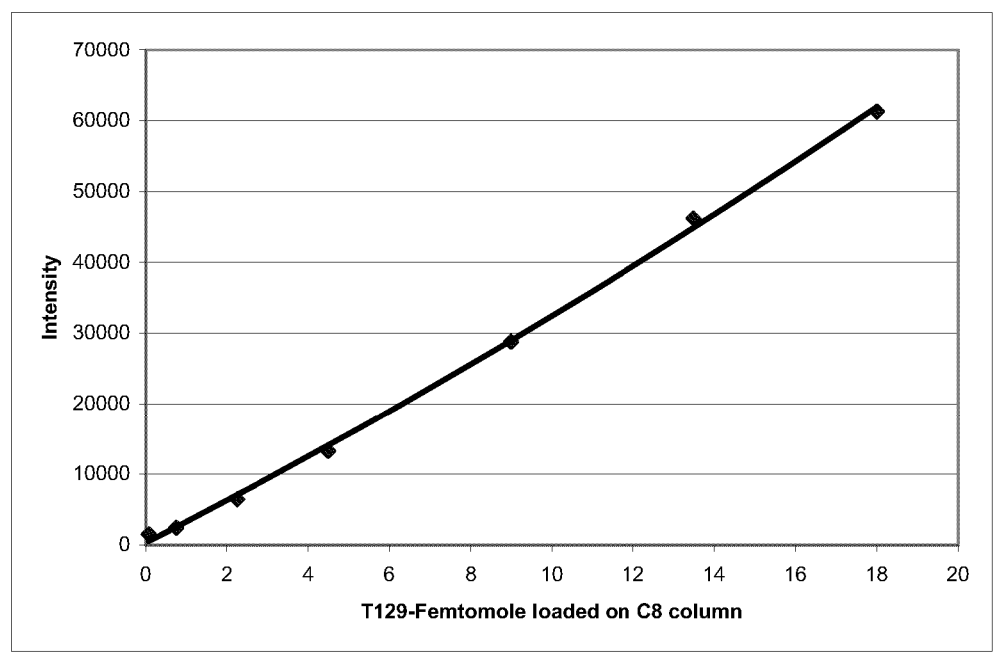
FIG. 6 shows the linearity of the quantitation of peptide T129 in serially diluted stock samples using an LC-MS/MS assay. The equation describing the trend line for FIG. 6 is as follows: $y = 26.919x^2 + 2939.4x + 310.78$. $R^2 = 0.9988$ for this fit. Details are described in Example 1.

Data collected and used to develop the LOQ and Calibration curves in FIGS. 5 and 6 is shown in Table 2.

TABLE 2

Data collected and used to develop LOQ and Calibration curves for peptide T129 in spiked stripped serum samples

| Peptide T129 Concentration (Attomoles/μl) | Femtomoles of peptide T129 in 30 μl sample | Average Ion Counts per Second | CV (%) |
|---|---|---|---|
| 2.5 | 0.075 | 1471.6 | 0.264429 |
| 25 | 0.75 | 2435.6 | 0.188653 |
| 75 | 2.25 | 6455.4 | 0.147946 |
| 150 | 4.5 | 13322.4 | 0.075327 |
| 300 | 9 | 28805 | 0.073374 |
| 450 | 13.5 | 46199.6 | 0.067088 |
| 600 | 18 | 61302.2 | 0.030893 |

Example 2

Demonstration of Quantitation of Peptide T129 in Peptide T129 Spiked Processed, Concentrated and Digested Stripped Serum A 500 μl sample of stripped serum (e.g., the test sample in this Example) was added atop the filter element of a commercially available 300 kDa molecular weight cut-off filter cartridge (Pall Corp. Nanosep 300 kDa, Pall Corp. Cat. No. OD300C33).

The test sample was completely filtered upon centrifugation of the cartridge at 13 kg for 6 minutes. The filtrate was removed and discarded. 500 μl of HPLC grade water was then added to the top of the filter and the cartridge was again centrifuged at 13 kg for 6 minutes. The filtrate was again removed and discarded. Next, 200 μl of 20 mM ammonium acetate was added to the top of the filter. The cartridge was again centrifuged at 13 kg for 3 minutes. The filtrate was again removed and discarded and 100 μl of 20 mM ammonium acetate was added to the top of the filter.

Then, 15 μg of trypsin (Promega Trypsin Gold, Mass Spec Grade, Promega Corp. Cat. No. V5280 or equivalent) was added to the test sample remaining on top of the filter. The resulting mixture was incubated without removal from the filter cartridge at 37 C for up to 17 hours.

After incubation, the filter cartridge was centrifuged at 13 kg for 6 minutes, and the filtrate retained. The filter cartridge was then washed by adding 50 μl of 20 mM ammonium acetate to the top of the filter and centrifuged at 13 kg for 6 minutes. Test samples for analysis by LC-MS/MS were created by pooling the two retained post-digestion filtrates.

The starting volume of stripped serum samples subjected to the above processing and concentration was about 500 μl. The final volume of each pooled post-digestion filtrate was about 130 μl. Thus the above process concentrates samples by a factor of 3.83.

Peptide T129 was then added to the pooled post-digestion filtrates in varying concentrations. 30 μl samples were then analyzed for quantitation of peptide T129 by LC-MS/MS according to the procedure described in Example 1 with the exception that the mass transitions shown in Table 3 were used. The fragment ion with a m/z of 797.4±0.5 was not used due to increased background generated by the processed, concentrated stripped serum.

TABLE 3

Mass transitions for precursor ions with m/z corresponding to peptide T129 from peptide T129 spiked stripped serum samples (Positive Polarity)

| Precursor Ion (m/z) | Fragment Ion (m/z) |
|---|---|
| 636.4 ± 0.5 | 912.4 ± 0.5 & 1059.5 ± 0.5 |

Figure 7:
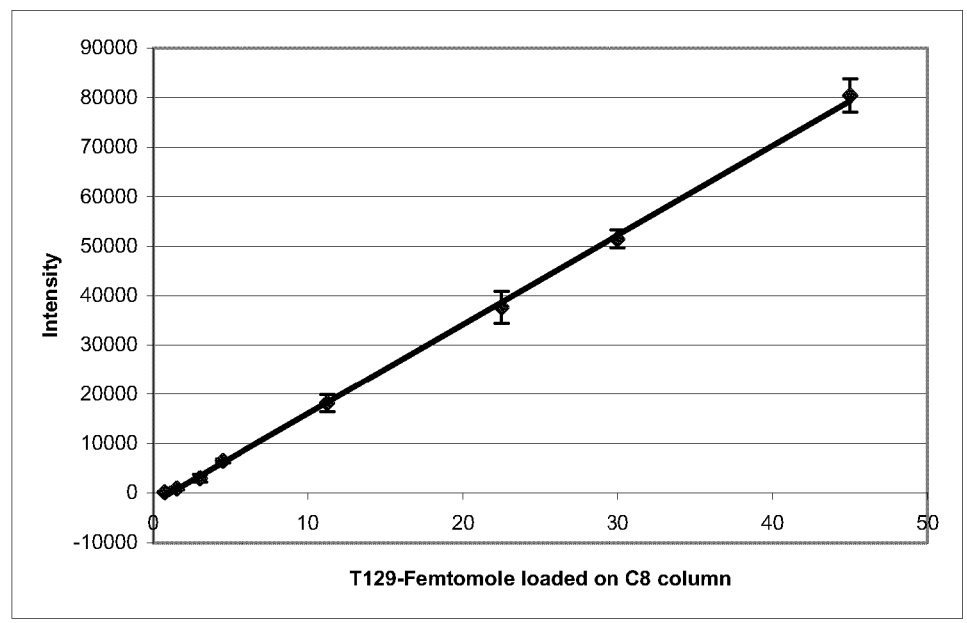
FIG. 7 shows the limit of quantitation verification for peptide T129 in stripped serum by MS/MS. The equation describing the trend line for FIG. 7 is as follows: $y = 1807.2x - 1975$. $R^2 = 0.9993$ for this fit. Details are described in Example 2.
Figure 8:
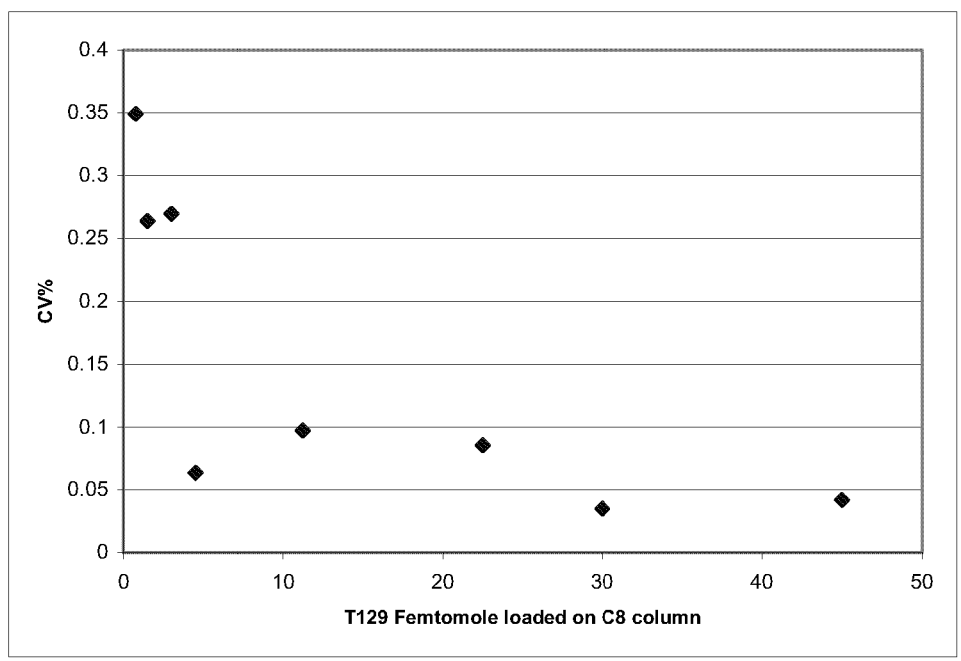
FIG. 8 shows the linearity of the quantitation of peptide T129 in peptide T129 spiked stripped serum using an LC-MS/MS assay. Details are described in Example 2.

Data collected and used to develop the LOQ and Calibration curves found in FIGS. 7 and 8 is shown in Table 4.

TABLE 4

Data collected and used to develop LOQ and Calibration curves for peptide T129

| Femtomoles of Tg in spiked serum sample | Average Ion Counts per Second | CV (%) |
|---|---|---|
| 0.75 | 203 | 0.348839 |
| 1.5 | 957.25 | 0.263782 |
| 3 | 2984.75 | 0.269659 |
| 4.5 | 6504.75 | 0.063318 |
| 11.25 | 18210.5 | 0.097296 |
| 22.5 | 37620 | 0.085823 |
| 30 | 51451 | 0.035083 |

Example 3

Demonstration of Quantitation of Peptide T129 in Stripped Serum Containing Various Concentrations of Added Tg Several 500 μl samples of stripped serum containing various concentrations of added Tg were prepared according to the procedure detailed in Example 2. LC-MS/MS of the resulting test samples was carried out following the steps detailed in Example 1.

Figure 9:
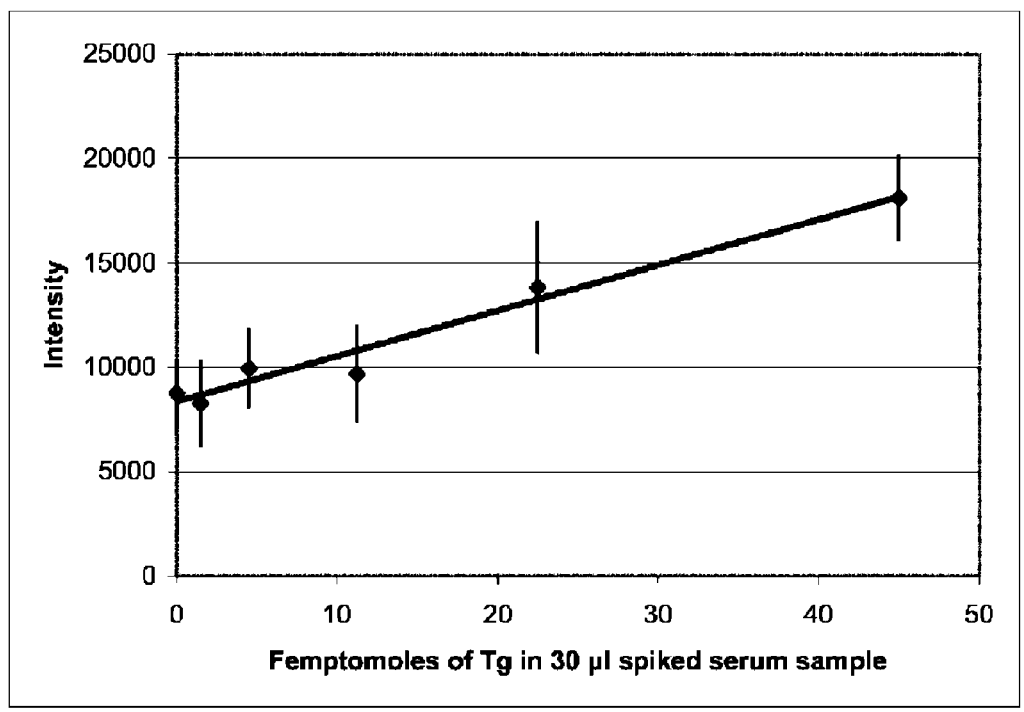
FIG. 9 shows the linearity of the quantitation of Tg peptide ions with m/z corresponding to peptide T129 using an LC-MS/MS assay in stripped serum spiked with Tg prior to processing and concentration according to the methods described herein. The equation describing the trend line for FIG. 9 is as follows: $y = 218.15x + 8363.2$. $R^2 = 0.9681$ for this fit. Details are described in Example 3.

Data collected and used to develop the calibration curve found in FIG. 9 are found in Table 6.

TABLE 6

Data collected and used to develop the calibration curve for peptide T129 MS/MS in Tg spiked stripped serum (processed and condensed as described in Example 3).

| Femtomoles of Tg in spiked serum sample | Average Ion Counts per Second | CV (%) |
|---|---|---|
| 0 | 8784.667 | 0.176987 |
| 1.5 | 8259.5 | 0.246833 |
| 4.5 | 9953.25 | 0.186588 |
| 11.25 | 9696.25 | 0.23816 |
| 22.5 | 13848.25 | 0.225496 |
| 45 | 18125.5 | 0.110826 |

The contents of the articles, patents, patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of thyroglobulin in a test sample, comprising:
   (a) digesting thyroglobulin from the test sample to form peptide T129;
   (b) ionizing the peptide T129 to generate a multiply charged ion detectable by mass spectrometry; wherein the ion has a mass/charge ratio (m/z) of 636.4±0.5; and
   (c) detecting the amount of one or more T129 fragment ions each having a m/z selected from the group consisting of 541.3±0.5, 612.3±0.5, 636.4±0.5, 726.4±0.5, 797.4±0.5, 912.4±0.5, and 1059.5±0.5 by mass spectrometry; wherein the amount of the ions detected is related to the amount of the thyroglobulin in the test sample.

2. The method of claim 1, wherein the mass spectrometry is tandem mass spectrometry.

3. The method of claim 1, wherein the detected T129 fragment ions each has a m/z selected from the group consisting of 797.4±0.5, 912.4±0.5, and 1059.5±0.5.

4. The method of claim 1, further comprising purifying the peptide T129 prior to ionizing the peptide T129.

5. The method of claim 4, wherein the purification is carried out with at least one size separation technique.

6. The method of claim 1, further comprising determining the baseline amount of endogenous peptide T129 in the test sample, wherein the baseline is subtracted from the amount of peptide T129 detected in the test sample before determining the amount of thyroglobulin in the test sample.

7. The method of claim 1, wherein the ionizing of step (b) comprises ionizing the peptide T129 to generate a multiply charged peptide T129 precursor ion detectable by mass spectrometry, and colliding the peptide T129 precursor ion with a collision gas to generate one or more peptide T129 fragment ions.

8. The method of claim 1, further comprising purifying thyroglobulin from a body fluid or tissue sample to generate a thyroglobulin containing test sample.

9. The method of claim 8, wherein the body fluid or tissue sample comprises plasma or serum.

10. The method of claim 1, wherein the test sample comprises a body fluid.

11. The method of claim 10, wherein the test sample comprises plasma or serum.

12. A method for determining persistence of thyroid tissue in a patient after surgical removal of the thyroid gland, the method comprising:
   (a) digesting thyroglobulin in a body fluid or tissue sample obtained from the patient to form peptide T129;
   (b) ionizing the peptide T129 to generate a multiply charged ion detectable by mass spectrometry; wherein the ion has a mass/charge ratio (m/z) of 636.4±0.5;
   (c) detecting the amount of one or more T129 fragment ions each having a m/z selected from the group consisting of 541.3±0.5, 612.3±0.5, 636.4±0.5, 726.4±0.5, 797.4±0.5, 912.4±0.5, and 1059.5±0.5 by mass spectrometry, wherein the presence of the one or more T129 fragment ions indicates persistence of thyroid tissue in the patient.

13. The method of claim 12, wherein the mass spectrometry is tandem mass spectrometry.

14. The method of claim 12, wherein the detected T129 fragment ions each has a m/z selected from the group consisting of 797.4±0.5, 912.4±0.5, and 1059.5±0.5.

15. The method of claim 12, further comprising purifying the peptide T129 prior to ionizing the peptide T129.

16. The method of claim 15, wherein the purification is carried out with at least one size separation technique.

17. The method of claim 12, further comprising determining the baseline amount of endogenous peptide T129 in the sample, wherein the baseline is subtracted from the amount of peptide T129 detected in the test sample before determining the presence of thyroglobulin in the sample.

18. The method of claim 12, wherein the ionizing of step (b) comprises ionizing the peptide T129 to generate a multiply charged peptide T129 precursor ion detectable by mass spectrometry, and colliding the peptide T129 precursor ion with a collision gas to generate one or more peptide T129 fragment ions.

19. The method of claim 12, further comprising purifying thyroglobulin from the body fluid or tissue sample to generate a thyroglobulin containing test sample.

20. The method of claim 12, wherein the body fluid or tissue sample comprises plasma or serum.

* * * * *

SEQUENCE LISTING

<160> NUMBER OF SEQ ID NOS: 4

<210> SEQ ID NO 1
<211> LENGTH: 2768
<212> TYPE: PRT
<213> ORGANISM: Homo sapiens

<400> SEQUENCE: 1

```
Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
        195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270

Glu Thr Thr Leu Tyr Arg Ile Leu Gln Arg Arg Phe Leu Ala Val Gln
        275                 280                 285

Ser Val Ile Ser Gly Arg Phe Arg Cys Pro Thr Lys Cys Glu Val Glu
    290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
            340                 345                 350

Gly Glu Pro Pro Ser Cys Ala Glu Gly Gln Ser Cys Ala Ser Glu Arg
        355                 360                 365
```

```
Gln Gln Ala Leu Ser Arg Leu Tyr Phe Gly Thr Ser Gly Tyr Phe Ser
    370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
        435                 440                 445

Pro Ser Arg Gly Leu Ala Arg Leu Ala Leu Gln Phe Thr Thr Asn Pro
    450                 455                 460

Lys Arg Leu Gln Gln Asn Leu Phe Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Phe Gln Gln Leu Gly Leu Ala Ser Phe Leu Asn Gly
            500                 505                 510

Gly Arg Gln Glu Asp Leu Ala Lys Pro Leu Ser Val Gly Leu Asp Ser
        515                 520                 525

Asn Ser Ser Thr Gly Thr Pro Glu Ala Ala Lys Lys Asp Gly Thr Met
    530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
                565                 570                 575

Phe Leu Leu Phe Leu Gln His Ala Ile Ser Val Pro Glu Asp Val Ala
            580                 585                 590

Arg Asp Leu Gly Asp Val Met Glu Thr Val Leu Ser Ser Gln Thr Cys
        595                 600                 605

Glu Gln Thr Pro Glu Arg Leu Phe Val Pro Ser Cys Thr Thr Glu Gly
    610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
                645                 650                 655

Arg Cys Pro Thr Asp Cys Glu Lys Gln Arg Ala Arg Met Gln Ser Leu
            660                 665                 670

Met Gly Ser Gln Pro Ala Gly Ser Thr Leu Phe Val Pro Ala Cys Thr
        675                 680                 685

Ser Glu Gly His Phe Leu Pro Val Gln Cys Phe Asn Ser Glu Cys Tyr
    690                 695                 700

Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
            740                 745                 750

Pro Thr Leu Ser Asp Thr Tyr Ile Pro Gln Cys Ser Thr Asp Gly Gln
        755                 760                 765

Trp Arg Gln Val Gln Cys Asn Gly Pro Pro Glu Gln Val Phe Glu Leu
    770                 775                 780

Tyr Gln Arg Trp Glu Ala Gln Asn Lys Gly Gln Asp Leu Thr Pro Ala
```

-continued

```
                785                 790                 795                 800
Lys Leu Leu Val Lys Ile Met Ser Tyr Arg Glu Ala Ala Ser Gly Asn
                    805                 810                 815

Phe Ser Leu Phe Ile Gln Ser Leu Tyr Glu Ala Gly Gln Gln Asp Val
                    820                 825                 830

Phe Pro Val Leu Ser Gln Tyr Pro Ser Leu Gln Asp Val Pro Leu Ala
                    835                 840                 845

Ala Leu Glu Gly Lys Arg Pro Gln Pro Arg Glu Asn Ile Leu Leu Glu
    850                 855                 860

Pro Tyr Leu Phe Trp Gln Ile Leu Asn Gly Gln Leu Ser Gln Tyr Pro
865                 870                 875                 880

Gly Ser Tyr Ser Asp Phe Ser Thr Pro Leu Ala His Phe Asp Leu Arg
                    885                 890                 895

Asn Cys Trp Cys Val Asp Glu Ala Gly Gln Glu Leu Glu Gly Met Arg
                    900                 905                 910

Ser Glu Pro Ser Lys Leu Pro Thr Cys Pro Gly Ser Cys Glu Glu Ala
                    915                 920                 925

Lys Leu Arg Val Leu Gln Phe Ile Arg Glu Thr Glu Glu Ile Val Ser
    930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
                    965                 970                 975

Pro Pro Arg Glu Ala Phe Ala Glu Gln Phe Leu Arg Gly Ser Asp Tyr
                    980                 985                 990

Ala Ile Arg Leu Ala Ala Gln Ser  Thr Leu Ser Phe Tyr  Gln Arg Arg
                    995                 1000                1005

Arg Phe  Ser Pro Asp Asp Ser  Ala Gly Ala Ser Ala  Leu Leu Arg
    1010                1015                1020

Ser Gly  Pro Tyr Met Pro Gln  Cys Asp Ala Phe Gly  Ser Trp Glu
    1025                1030                1035

Pro Val  Gln Cys His Ala Gly  Thr Gly His Cys Trp  Cys Val Asp
    1040                1045                1050

Glu Lys  Gly Gly Phe Ile Pro  Gly Ser Leu Thr Ala  Arg Ser Leu
    1055                1060                1065

Gln Ile  Pro Gln Cys Pro Thr  Thr Cys Glu Lys Ser  Arg Thr Ser
    1070                1075                1080

Gly Leu  Leu Ser Ser Trp Lys  Gln Ala Arg Ser Gln  Glu Asn Pro
    1085                1090                1095

Ser Pro  Lys Asp Leu Phe Val  Pro Ala Cys Leu Glu  Thr Gly Glu
    1100                1105                1110

Tyr Ala  Arg Leu Gln Ala Ser  Gly Ala Gly Thr Trp  Cys Val Asp
    1115                1120                1125

Pro Ala  Ser Gly Glu Glu Leu  Arg Pro Gly Ser Ser  Ser Ser Ala
    1130                1135                1140

Gln Cys  Pro Ser Leu Cys Asn  Val Leu Lys Ser Gly  Val Leu Ser
    1145                1150                1155

Arg Arg  Val Ser Pro Gly Tyr  Val Pro Ala Cys Arg  Ala Glu Asp
    1160                1165                1170

Gly Gly  Phe Ser Pro Val Gln  Cys Asp Gln Ala Gln  Gly Ser Cys
    1175                1180                1185

Trp Cys  Val Met Asp Ser Gly  Glu Glu Val Pro Gly  Thr Arg Val
    1190                1195                1200
```

-continued

| | | | | | | | | | |
|---|---|---|---|---|---|---|---|---|---|
|Thr|Gly|Gly|Gln|Pro|Ala|Cys|Glu|Ser|Pro|Arg|Cys|Pro|Leu|Pro|
|1205| | | | |1210| | | |1215|

Phe Asn Ala Ser Glu Val Val Gly Gly Thr Ile Leu Cys Glu Thr
1220                          1225                     1230

Ile Ser Gly Pro Thr Gly Ser Ala Met Gln Gln Cys Gln Leu Leu
1235                          1240                     1245

Cys Arg Gln Gly Ser Trp Ser Val Phe Pro Pro Gly Pro Leu Ile
1250                          1255                     1260

Cys Ser Leu Glu Ser Gly Arg Trp Glu Ser Gln Leu Pro Gln Pro
1265                          1270                     1275

Arg Ala Cys Gln Arg Pro Gln Leu Trp Gln Thr Ile Gln Thr Gln
1280                          1285                     1290

Gly His Phe Gln Leu Gln Leu Pro Pro Gly Lys Met Cys Ser Ala
1295                          1300                     1305

Asp Tyr Ala Asp Leu Leu Gln Thr Phe Gln Val Phe Ile Leu Asp
1310                          1315                     1320

Glu Leu Thr Ala Arg Gly Phe Cys Gln Ile Gln Val Lys Thr Phe
1325                          1330                     1335

Gly Thr Leu Val Ser Ile Pro Val Cys Asn Asn Ser Ser Val Gln
1340                          1345                     1350

Val Gly Cys Leu Thr Arg Glu Arg Leu Gly Val Asn Val Thr Trp
1355                          1360                     1365

Lys Ser Arg Leu Glu Asp Ile Pro Val Ala Ser Leu Pro Asp Leu
1370                          1375                     1380

His Asp Ile Glu Arg Ala Leu Val Gly Lys Asp Leu Leu Gly Arg
1385                          1390                     1395

Phe Thr Asp Leu Ile Gln Ser Gly Ser Phe Gln Leu His Leu Asp
1400                          1405                     1410

Ser Lys Thr Phe Pro Ala Glu Thr Ile Arg Phe Leu Gln Gly Asp
1415                          1420                     1425

His Phe Gly Thr Ser Pro Arg Thr Trp Phe Gly Cys Ser Glu Gly
1430                          1435                     1440

Phe Tyr Gln Val Leu Thr Ser Glu Ala Ser Gln Asp Gly Leu Gly
1445                          1450                     1455

Cys Val Lys Cys Pro Glu Gly Ser Tyr Ser Gln Asp Glu Glu Cys
1460                          1465                     1470

Ile Pro Cys Pro Val Gly Phe Tyr Gln Glu Gln Ala Gly Ser Leu
1475                          1480                     1485

Ala Cys Val Pro Cys Pro Val Gly Arg Thr Thr Ile Ser Ala Gly
1490                          1495                     1500

Ala Phe Ser Gln Thr His Cys Val Thr Asp Cys Gln Arg Asn Glu
1505                          1510                     1515

Ala Gly Leu Gln Cys Asp Gln Asn Gly Gln Tyr Arg Ala Ser Gln
1520                          1525                     1530

Lys Asp Arg Gly Ser Gly Lys Ala Phe Cys Val Asp Gly Glu Gly
1535                          1540                     1545

Arg Arg Leu Pro Trp Trp Glu Thr Glu Ala Pro Leu Glu Asp Ser
1550                          1555                     1560

Gln Cys Leu Met Met Gln Lys Phe Glu Lys Val Pro Glu Ser Lys
1565                          1570                     1575

Val Ile Phe Asp Ala Asn Ala Pro Val Ala Val Arg Ser Lys Val
1580                          1585                     1590

Pro Asp Ser Glu Phe Pro Val Met Gln Cys Leu Thr Asp Cys Thr
1595                          1600                     1605

-continued

```
Glu Asp Glu Ala Cys Ser Phe Phe Thr Val Ser Thr Thr Glu Pro
    1610            1615                1620

Glu Ile Ser Cys Asp Phe Tyr Ala Trp Thr Ser Asp Asn Val Ala
    1625            1630                1635

Cys Met Thr Ser Asp Gln Lys Arg Asp Ala Leu Gly Asn Ser Lys
    1640            1645                1650

Ala Thr Ser Phe Gly Ser Leu Arg Cys Gln Val Lys Val Arg Ser
    1655            1660                1665

His Gly Gln Asp Ser Pro Ala Val Tyr Leu Lys Lys Gly Gln Gly
    1670            1675                1680

Ser Thr Thr Thr Leu Gln Lys Arg Phe Glu Pro Thr Gly Phe Gln
    1685            1690                1695

Asn Met Leu Ser Gly Leu Tyr Asn Pro Ile Val Phe Ser Ala Ser
    1700            1705                1710

Gly Ala Asn Leu Thr Asp Ala His Leu Phe Cys Leu Leu Ala Cys
    1715            1720                1725

Asp Arg Asp Leu Cys Cys Asp Gly Phe Val Leu Thr Gln Val Gln
    1730            1735                1740

Gly Gly Ala Ile Ile Cys Gly Leu Leu Ser Ser Pro Ser Val Leu
    1745            1750                1755

Leu Cys Asn Val Lys Asp Trp Met Asp Pro Ser Glu Ala Trp Ala
    1760            1765                1770

Asn Ala Thr Cys Pro Gly Val Thr Tyr Asp Gln Glu Ser His Gln
    1775            1780                1785

Val Ile Leu Arg Leu Gly Asp Gln Glu Phe Ile Lys Ser Leu Thr
    1790            1795                1800

Pro Leu Glu Gly Thr Gln Asp Thr Phe Thr Asn Phe Gln Gln Val
    1805            1810                1815

Tyr Leu Trp Lys Asp Ser Asp Met Gly Ser Arg Pro Glu Ser Met
    1820            1825                1830

Gly Cys Arg Lys Asp Thr Val Pro Arg Pro Ala Ser Pro Thr Glu
    1835            1840                1845

Ala Gly Leu Thr Thr Glu Leu Phe Ser Pro Val Asp Leu Asn Gln
    1850            1855                1860

Val Ile Val Asn Gly Asn Gln Ser Leu Ser Ser Gln Lys His Trp
    1865            1870                1875

Leu Phe Lys His Leu Phe Ser Ala Gln Gln Ala Asn Leu Trp Cys
    1880            1885                1890

Leu Ser Arg Cys Val Gln Glu His Ser Phe Cys Gln Leu Ala Glu
    1895            1900                1905

Ile Thr Glu Ser Ala Ser Leu Tyr Phe Thr Cys Thr Leu Tyr Pro
    1910            1915                1920

Glu Ala Gln Val Cys Asp Asp Ile Met Glu Ser Asn Ala Gln Gly
    1925            1930                1935

Cys Arg Leu Ile Leu Pro Gln Met Pro Lys Ala Leu Phe Arg Lys
    1940            1945                1950

Lys Val Ile Leu Glu Asp Lys Val Lys Asn Phe Tyr Thr Arg Leu
    1955            1960                1965

Pro Phe Gln Lys Leu Met Gly Ile Ser Ile Arg Asn Lys Val Pro
    1970            1975                1980

Met Ser Glu Lys Ser Ile Ser Asn Gly Phe Phe Glu Cys Glu Arg
    1985            1990                1995

Arg Cys Asp Ala Asp Pro Cys Cys Thr Gly Phe Gly Phe Leu Asn
```

-continued

```
             2000                2005                2010
Val  Ser  Gln  Leu  Lys  Gly  Gly  Glu  Val  Thr  Cys  Leu  Thr  Leu  Asn
     2015                2020                2025
Ser  Leu  Gly  Ile  Gln  Met  Cys  Ser  Glu  Glu  Asn  Gly  Gly  Ala  Trp
     2030                2035                2040
Arg  Ile  Leu  Asp  Cys  Gly  Ser  Pro  Asp  Ile  Glu  Val  His  Thr  Tyr
     2045                2050                2055
Pro  Phe  Gly  Trp  Tyr  Gln  Lys  Pro  Ile  Ala  Gln  Asn  Asn  Ala  Pro
     2060                2065                2070
Ser  Phe  Cys  Pro  Leu  Val  Val  Leu  Pro  Ser  Leu  Thr  Glu  Lys  Val
     2075                2080                2085
Ser  Leu  Asp  Ser  Trp  Gln  Ser  Leu  Ala  Leu  Ser  Ser  Val  Val  Val
     2090                2095                2100
Asp  Pro  Ser  Ile  Arg  His  Phe  Asp  Val  Ala  His  Val  Ser  Thr  Ala
     2105                2110                2115
Ala  Thr  Ser  Asn  Phe  Ser  Ala  Val  Arg  Asp  Leu  Cys  Leu  Ser  Glu
     2120                2125                2130
Cys  Ser  Gln  His  Glu  Ala  Cys  Leu  Ile  Thr  Thr  Leu  Gln  Thr  Gln
     2135                2140                2145
Pro  Gly  Ala  Val  Arg  Cys  Met  Phe  Tyr  Ala  Asp  Thr  Gln  Ser  Cys
     2150                2155                2160
Thr  His  Ser  Leu  Gln  Gly  Gln  Asn  Cys  Arg  Leu  Leu  Leu  Arg  Glu
     2165                2170                2175
Glu  Ala  Thr  His  Ile  Tyr  Arg  Lys  Pro  Gly  Ile  Ser  Leu  Leu  Ser
     2180                2185                2190
Tyr  Glu  Ala  Ser  Val  Pro  Ser  Val  Pro  Ile  Ser  Thr  His  Gly  Arg
     2195                2200                2205
Leu  Leu  Gly  Arg  Ser  Gln  Ala  Ile  Gln  Val  Gly  Thr  Ser  Trp  Lys
     2210                2215                2220
Gln  Val  Asp  Gln  Phe  Leu  Gly  Val  Pro  Tyr  Ala  Ala  Pro  Pro  Leu
     2225                2230                2235
Ala  Glu  Arg  Arg  Phe  Gln  Ala  Pro  Glu  Pro  Leu  Asn  Trp  Thr  Gly
     2240                2245                2250
Ser  Trp  Asp  Ala  Ser  Lys  Pro  Arg  Ala  Ser  Cys  Trp  Gln  Pro  Gly
     2255                2260                2265
Thr  Arg  Thr  Ser  Thr  Ser  Pro  Gly  Val  Ser  Glu  Asp  Cys  Leu  Tyr
     2270                2275                2280
Leu  Asn  Val  Phe  Ile  Pro  Gln  Asn  Val  Ala  Pro  Asn  Ala  Ser  Val
     2285                2290                2295
Leu  Val  Phe  Phe  His  Asn  Thr  Met  Asp  Arg  Glu  Glu  Ser  Glu  Gly
     2300                2305                2310
Trp  Pro  Ala  Ile  Asp  Gly  Ser  Phe  Leu  Ala  Ala  Val  Gly  Asn  Leu
     2315                2320                2325
Ile  Val  Val  Thr  Ala  Ser  Tyr  Arg  Val  Gly  Val  Phe  Gly  Phe  Leu
     2330                2335                2340
Ser  Ser  Gly  Ser  Gly  Glu  Val  Ser  Gly  Asn  Trp  Gly  Leu  Leu  Asp
     2345                2350                2355
Gln  Val  Ala  Ala  Leu  Thr  Trp  Val  Gln  Thr  His  Ile  Arg  Gly  Phe
     2360                2365                2370
Gly  Gly  Asp  Pro  Arg  Arg  Val  Ser  Leu  Ala  Ala  Asp  Arg  Gly  Gly
     2375                2380                2385
Ala  Asp  Val  Ala  Ser  Ile  His  Leu  Leu  Thr  Ala  Arg  Ala  Thr  Asn
     2390                2395                2400
```

```
Ser Gln Leu Phe Arg Arg Ala Val Leu Met Gly Gly Ser Ala Leu
    2405                2410                2415

Ser Pro Ala Ala Val Ile Ser His Glu Arg Ala Gln Gln Gln Ala
    2420                2425                2430

Ile Ala Leu Ala Lys Glu Val Ser Cys Pro Met Ser Ser Ser Gln
    2435                2440                2445

Glu Val Val Ser Cys Leu Arg Gln Lys Pro Ala Asn Val Leu Asn
    2450                2455                2460

Asp Ala Gln Thr Lys Leu Leu Ala Val Ser Gly Pro Phe His Tyr
    2465                2470                2475

Trp Gly Pro Val Ile Asp Gly His Phe Leu Arg Glu Pro Pro Ala
    2480                2485                2490

Arg Ala Leu Lys Arg Ser Leu Trp Val Glu Val Asp Leu Leu Ile
    2495                2500                2505

Gly Ser Ser Gln Asp Asp Gly Leu Ile Asn Arg Ala Lys Ala Val
    2510                2515                2520

Lys Gln Phe Glu Glu Ser Arg Gly Arg Thr Ser Ser Lys Thr Ala
    2525                2530                2535

Phe Tyr Gln Ala Leu Gln Asn Ser Leu Gly Gly Glu Asp Ser Asp
    2540                2545                2550

Ala Arg Val Glu Ala Ala Ala Thr Trp Tyr Tyr Ser Leu Glu His
    2555                2560                2565

Ser Thr Asp Asp Tyr Ala Ser Phe Ser Arg Ala Leu Glu Asn Ala
    2570                2575                2580

Thr Arg Asp Tyr Phe Ile Ile Cys Pro Ile Ile Asp Met Ala Ser
    2585                2590                2595

Ala Trp Ala Lys Arg Ala Arg Gly Asn Val Phe Met Tyr His Ala
    2600                2605                2610

Pro Glu Asn Tyr Gly His Gly Ser Leu Glu Leu Leu Ala Asp Val
    2615                2620                2625

Gln Phe Ala Leu Gly Leu Pro Phe Tyr Pro Ala Tyr Glu Gly Gln
    2630                2635                2640

Phe Ser Leu Glu Glu Lys Ser Leu Ser Leu Lys Ile Met Gln Tyr
    2645                2650                2655

Phe Ser His Phe Ile Arg Ser Gly Asn Pro Asn Tyr Pro Tyr Glu
    2660                2665                2670

Phe Ser Arg Lys Val Pro Thr Phe Ala Thr Pro Trp Pro Asp Phe
    2675                2680                2685

Val Pro Arg Ala Gly Gly Glu Asn Tyr Lys Glu Phe Ser Glu Leu
    2690                2695                2700

Leu Pro Asn Arg Gln Gly Leu Lys Lys Ala Asp Cys Ser Phe Trp
    2705                2710                2715

Ser Lys Tyr Ile Ser Ser Leu Lys Thr Ser Ala Asp Gly Ala Lys
    2720                2725                2730

Gly Gly Gln Ser Ala Glu Ser Glu Glu Glu Leu Thr Ala Gly
    2735                2740                2745

Ser Gly Leu Arg Glu Asp Leu Leu Ser Leu Gln Glu Pro Gly Ser
    2750                2755                2760

Lys Thr Tyr Ser Lys
    2765

<210> SEQ ID NO 2
<211> LENGTH: 2711
<212> TYPE: PRT
<213> ORGANISM: Homo sapiens
```

<400> SEQUENCE: 2

```
Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
        195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270

Glu Thr Thr Leu Tyr Arg Ile Leu Gln Arg Arg Phe Leu Ala Val Gln
        275                 280                 285

Ser Val Ile Ser Gly Arg Phe Arg Cys Pro Thr Lys Cys Glu Val Glu
    290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
            340                 345                 350

Gly Glu Pro Pro Ser Cys Ala Glu Gly Gln Ser Cys Ala Ser Glu Arg
        355                 360                 365

Gln Gln Ala Leu Ser Arg Leu Tyr Phe Gly Thr Ser Gly Tyr Phe Ser
    370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415
```

```
Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
            435                 440                 445

Pro Ser Arg Gly Leu Ala Arg Leu Ala Leu Gln Phe Thr Thr Asn Pro
450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Phe Gln Leu Gly Leu Ala Ser Phe Leu Asn Gly
                500                 505                 510

Gly Arg Gln Glu Asp Leu Ala Lys Pro Leu Ser Val Gly Leu Asp Ser
            515                 520                 525

Asn Ser Ser Thr Gly Thr Pro Glu Ala Ala Lys Lys Asp Gly Thr Met
530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
                565                 570                 575

Phe Leu Leu Phe Leu Gln His Ala Ile Ser Val Pro Glu Asp Val Ala
            580                 585                 590

Arg Asp Leu Gly Asp Val Met Glu Thr Val Leu Ser Ser Gln Thr Cys
            595                 600                 605

Glu Gln Thr Pro Glu Arg Leu Phe Val Pro Ser Cys Thr Thr Glu Gly
            610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
                645                 650                 655

Arg Cys Pro Thr Asp Cys Glu Lys Gln Arg Ala Arg Met Gln Ser Leu
            660                 665                 670

Met Gly Ser Gln Pro Ala Gly Ser Thr Leu Phe Val Pro Ala Cys Thr
            675                 680                 685

Ser Glu Gly His Phe Leu Pro Val Gln Cys Phe Asn Ser Glu Cys Tyr
            690                 695                 700

Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
            740                 745                 750

Pro Thr Leu Ser Asp Thr Tyr Ile Pro Gln Cys Ser Thr Asp Gly Gln
            755                 760                 765

Trp Arg Gln Val Gln Cys Asn Gly Pro Pro Glu Gln Val Phe Glu Leu
            770                 775                 780

Tyr Gln Arg Trp Glu Ala Gln Asn Lys Gly Gln Asp Leu Thr Pro Ala
785                 790                 795                 800

Lys Leu Leu Val Lys Ile Met Ser Tyr Arg Glu Ala Ala Ser Gly Asn
                805                 810                 815

Phe Ser Leu Phe Ile Gln Ser Leu Tyr Glu Ala Gly Gln Gln Asp Val
            820                 825                 830

Phe Pro Val Leu Ser Gln Tyr Pro Ser Leu Gln Asp Val Pro Leu Ala
```

-continued

```
                835                 840                 845
Ala Leu Glu Gly Lys Arg Pro Gln Pro Arg Glu Asn Ile Leu Leu Glu
850                 855                 860
Pro Tyr Leu Phe Trp Gln Ile Leu Asn Gly Gln Leu Ser Gln Tyr Pro
865                 870                 875                 880
Gly Ser Tyr Ser Asp Phe Ser Thr Pro Leu Ala His Phe Asp Leu Arg
                885                 890                 895
Asn Cys Trp Cys Val Asp Glu Ala Gly Gln Glu Leu Glu Gly Met Arg
                900                 905                 910
Ser Glu Pro Ser Lys Leu Pro Thr Cys Pro Gly Ser Cys Glu Glu Ala
                915                 920                 925
Lys Leu Arg Val Leu Gln Phe Ile Arg Glu Thr Glu Glu Ile Val Ser
                930                 935                 940
Ala Ser Asn Ser Ser Arg Phe Pro Leu Gly Glu Ser Phe Leu Val Ala
945                 950                 955                 960
Lys Gly Ile Arg Leu Arg Asn Glu Asp Leu Gly Leu Pro Pro Leu Phe
                965                 970                 975
Pro Pro Arg Glu Ala Phe Ala Glu Gln Phe Leu Arg Gly Ser Asp Tyr
                980                 985                 990
Ala Ile Arg Leu Ala Ala Gln Ser Thr Leu Ser Phe Tyr Gln Arg Arg
                995                 1000                1005
Arg Phe Ser Pro Asp Asp Ser Ala Gly Ala Ser Ala Leu Leu Arg
     1010                1015                1020
Ser Gly Pro Tyr Met Pro Gln Cys Asp Ala Phe Gly Ser Trp Glu
     1025                1030                1035
Pro Val Gln Cys His Ala Gly Thr Gly His Cys Trp Cys Val Asp
     1040                1045                1050
Glu Lys Gly Gly Phe Ile Pro Gly Ser Leu Thr Ala Arg Ser Leu
     1055                1060                1065
Gln Ile Pro Gln Cys Pro Thr Thr Cys Glu Lys Ser Arg Thr Ser
     1070                1075                1080
Gly Leu Leu Ser Ser Trp Lys Gln Ala Arg Ser Gln Glu Asn Pro
     1085                1090                1095
Ser Pro Lys Asp Leu Phe Val Pro Ala Cys Leu Glu Thr Gly Glu
     1100                1105                1110
Tyr Ala Arg Leu Gln Ala Ser Gly Ala Gly Thr Trp Cys Val Asp
     1115                1120                1125
Pro Ala Ser Gly Glu Glu Leu Arg Pro Gly Ser Ser Ser Ser Ala
     1130                1135                1140
Gln Cys Pro Ser Leu Cys Asn Val Leu Lys Ser Gly Val Leu Ser
     1145                1150                1155
Arg Arg Val Ser Pro Gly Tyr Val Pro Ala Cys Arg Ala Glu Asp
     1160                1165                1170
Gly Gly Phe Ser Pro Val Gln Cys Asp Gln Ala Gln Gly Ser Cys
     1175                1180                1185
Trp Cys Val Met Asp Ser Gly Glu Glu Val Pro Gly Thr Arg Val
     1190                1195                1200
Thr Gly Gly Gln Pro Ala Cys Glu Ser Pro Arg Cys Pro Leu Pro
     1205                1210                1215
Phe Asn Ala Ser Glu Val Val Gly Gly Thr Ile Leu Cys Glu Thr
     1220                1225                1230
Ile Ser Gly Pro Thr Gly Ser Ala Met Gln Gln Cys Gln Leu Leu
     1235                1240                1245
```

-continued

```
Cys Arg Gln Gly Ser Trp Ser Val Phe Pro Gly Pro Leu Ile
1250                1255                1260

Cys Ser Leu Glu Ser Gly Arg Trp Glu Ser Gln Leu Pro Gln Pro
1265                1270                1275

Arg Ala Cys Gln Arg Pro Gln Leu Trp Gln Thr Ile Gln Thr Gln
1280                1285                1290

Gly His Phe Gln Leu Gln Leu Pro Pro Gly Lys Met Cys Ser Ala
1295                1300                1305

Asp Tyr Ala Asp Leu Leu Gln Thr Phe Gln Val Phe Ile Leu Asp
1310                1315                1320

Glu Leu Thr Ala Arg Gly Phe Cys Gln Ile Gln Val Lys Thr Phe
1325                1330                1335

Gly Thr Leu Val Ser Ile Pro Val Cys Asn Asn Ser Ser Val Gln
1340                1345                1350

Val Gly Cys Leu Thr Arg Glu Arg Leu Gly Val Asn Val Thr Trp
1355                1360                1365

Lys Ser Arg Leu Glu Asp Ile Pro Val Ala Ser Leu Pro Asp Leu
1370                1375                1380

His Asp Ile Glu Arg Ala Leu Val Gly Lys Asp Leu Leu Gly Arg
1385                1390                1395

Phe Thr Asp Leu Ile Gln Ser Gly Ser Phe Gln Leu His Leu Asp
1400                1405                1410

Ser Lys Thr Phe Pro Ala Glu Thr Ile Arg Phe Leu Gln Gly Asp
1415                1420                1425

His Phe Gly Thr Ser Pro Arg Thr Trp Phe Gly Cys Ser Glu Gly
1430                1435                1440

Phe Tyr Gln Val Leu Thr Ser Glu Ala Ser Gln Asp Gly Leu Gly
1445                1450                1455

Cys Val Lys Cys Pro Glu Gly Ser Tyr Ser Gln Asp Glu Glu Cys
1460                1465                1470

Ile Pro Cys Pro Val Gly Phe Tyr Gln Glu Gln Ala Gly Ser Leu
1475                1480                1485

Ala Cys Val Pro Cys Pro Val Gly Arg Thr Thr Ile Ser Ala Gly
1490                1495                1500

Ala Phe Ser Gln Thr His Leu Met Gln Lys Phe Glu Lys Val Pro
1505                1510                1515

Glu Ser Lys Val Ile Phe Asp Ala Asn Ala Pro Val Ala Val Arg
1520                1525                1530

Ser Lys Val Pro Asp Ser Glu Phe Pro Val Met Gln Cys Leu Thr
1535                1540                1545

Asp Cys Thr Glu Asp Glu Ala Cys Ser Phe Phe Thr Val Ser Thr
1550                1555                1560

Thr Glu Pro Glu Ile Ser Cys Asp Phe Tyr Ala Trp Thr Ser Asp
1565                1570                1575

Asn Val Ala Cys Met Thr Ser Asp Gln Lys Arg Asp Ala Leu Gly
1580                1585                1590

Asn Ser Lys Ala Thr Ser Phe Gly Ser Leu Arg Cys Gln Val Lys
1595                1600                1605

Val Arg Ser His Gly Gln Asp Ser Pro Ala Val Tyr Leu Lys Lys
1610                1615                1620

Gly Gln Gly Ser Thr Thr Thr Leu Gln Lys Arg Phe Glu Pro Thr
1625                1630                1635

Gly Phe Gln Asn Met Leu Ser Gly Leu Tyr Asn Pro Ile Val Phe
1640                1645                1650
```

-continued

Ser Ala Ser Gly Ala Asn Leu Thr Asp Ala His Leu Phe Cys Leu
    1655            1660            1665

Leu Ala Cys Asp Arg Asp Leu Cys Cys Asp Gly Phe Val Leu Thr
    1670            1675            1680

Gln Val Gln Gly Gly Ala Ile Ile Cys Gly Leu Leu Ser Ser Pro
    1685            1690            1695

Ser Val Leu Leu Cys Asn Val Lys Asp Trp Met Asp Pro Ser Glu
    1700            1705            1710

Ala Trp Ala Asn Ala Thr Cys Pro Gly Val Thr Tyr Asp Gln Glu
    1715            1720            1725

Ser His Gln Val Ile Leu Arg Leu Gly Asp Gln Glu Phe Ile Lys
    1730            1735            1740

Ser Leu Thr Pro Leu Glu Gly Thr Gln Asp Thr Phe Thr Asn Phe
    1745            1750            1755

Gln Gln Val Tyr Leu Trp Lys Asp Ser Asp Met Gly Ser Arg Pro
    1760            1765            1770

Glu Ser Met Gly Cys Arg Lys Asp Thr Val Pro Arg Pro Ala Ser
    1775            1780            1785

Pro Thr Glu Ala Gly Leu Thr Thr Glu Leu Phe Ser Pro Val Asp
    1790            1795            1800

Leu Asn Gln Val Ile Val Asn Gly Asn Gln Ser Leu Ser Ser Gln
    1805            1810            1815

Lys His Trp Leu Phe Lys His Leu Phe Ser Ala Gln Gln Ala Asn
    1820            1825            1830

Leu Trp Cys Leu Ser Arg Cys Val Gln Glu His Ser Phe Cys Gln
    1835            1840            1845

Leu Ala Glu Ile Thr Glu Ser Ala Ser Leu Tyr Phe Thr Cys Thr
    1850            1855            1860

Leu Tyr Pro Glu Ala Gln Val Cys Asp Asp Ile Met Glu Ser Asn
    1865            1870            1875

Ala Gln Gly Cys Arg Leu Ile Leu Pro Gln Met Pro Lys Ala Leu
    1880            1885            1890

Phe Arg Lys Lys Val Ile Leu Glu Asp Lys Val Lys Asn Phe Tyr
    1895            1900            1905

Thr Arg Leu Pro Phe Gln Lys Leu Met Gly Ile Ser Ile Arg Asn
    1910            1915            1920

Lys Val Pro Met Ser Glu Lys Ser Ile Ser Asn Gly Phe Phe Glu
    1925            1930            1935

Cys Glu Arg Arg Cys Asp Ala Asp Pro Cys Cys Thr Gly Phe Gly
    1940            1945            1950

Phe Leu Asn Val Ser Gln Leu Lys Gly Gly Glu Val Thr Cys Leu
    1955            1960            1965

Thr Leu Asn Ser Leu Gly Ile Gln Met Cys Ser Glu Glu Asn Gly
    1970            1975            1980

Gly Ala Trp Arg Ile Leu Asp Cys Gly Ser Pro Asp Ile Glu Val
    1985            1990            1995

His Thr Tyr Pro Phe Gly Trp Tyr Gln Lys Pro Ile Ala Gln Asn
    2000            2005            2010

Asn Ala Pro Ser Phe Cys Pro Leu Val Val Leu Pro Ser Leu Thr
    2015            2020            2025

Glu Lys Val Ser Leu Asp Ser Trp Gln Ser Leu Ala Leu Ser Ser
    2030            2035            2040

Val Val Val Asp Pro Ser Ile Arg His Phe Asp Val Ala His Val

-continued

```
            2045                2050                2055

Ser Thr Ala Ala Thr Ser Asn Phe Ser Ala Val Arg Asp Leu Cys
2060                2065                2070

Leu Ser Glu Cys Ser Gln His Glu Ala Cys Leu Ile Thr Thr Leu
2075                2080                2085

Gln Thr Gln Pro Gly Ala Val Arg Cys Met Phe Tyr Ala Asp Thr
2090                2095                2100

Gln Ser Cys Thr His Ser Leu Gln Gly Gln Asn Cys Arg Leu Leu
2105                2110                2115

Leu Arg Glu Glu Ala Thr His Ile Tyr Arg Lys Pro Gly Ile Ser
2120                2125                2130

Leu Leu Ser Tyr Glu Ala Ser Val Pro Ser Val Pro Ile Ser Thr
2135                2140                2145

His Gly Arg Leu Leu Gly Arg Ser Gln Ala Ile Gln Val Gly Thr
2150                2155                2160

Ser Trp Lys Gln Val Asp Gln Phe Leu Gly Val Pro Tyr Ala Ala
2165                2170                2175

Pro Pro Leu Ala Glu Arg Arg Phe Gln Ala Pro Glu Pro Leu Asn
2180                2185                2190

Trp Thr Gly Ser Trp Asp Ala Ser Lys Pro Arg Ala Ser Cys Trp
2195                2200                2205

Gln Pro Gly Thr Arg Thr Ser Thr Ser Pro Gly Val Ser Glu Asp
2210                2215                2220

Cys Leu Tyr Leu Asn Val Phe Ile Pro Gln Asn Val Ala Pro Asn
2225                2230                2235

Ala Ser Val Leu Val Phe Phe His Asn Thr Met Asp Arg Glu Glu
2240                2245                2250

Ser Glu Gly Trp Pro Ala Ile Asp Gly Ser Phe Leu Ala Ala Val
2255                2260                2265

Gly Asn Leu Ile Val Val Thr Ala Ser Tyr Arg Val Gly Val Phe
2270                2275                2280

Gly Phe Leu Ser Ser Gly Ser Gly Glu Val Ser Gly Asn Trp Gly
2285                2290                2295

Leu Leu Asp Gln Val Ala Ala Leu Thr Trp Val Gln Thr His Ile
2300                2305                2310

Arg Gly Phe Gly Gly Asp Pro Arg Arg Val Ser Leu Ala Ala Asp
2315                2320                2325

Arg Gly Gly Ala Asp Val Ala Ser Ile His Leu Leu Thr Ala Arg
2330                2335                2340

Ala Thr Asn Ser Gln Leu Phe Arg Arg Ala Val Leu Met Gly Gly
2345                2350                2355

Ser Ala Leu Ser Pro Ala Ala Val Ile Ser His Glu Arg Ala Gln
2360                2365                2370

Gln Gln Ala Ile Ala Leu Ala Lys Glu Val Ser Cys Pro Met Ser
2375                2380                2385

Ser Ser Gln Glu Val Val Ser Cys Leu Arg Gln Lys Pro Ala Asn
2390                2395                2400

Val Leu Asn Asp Ala Gln Thr Lys Leu Leu Ala Val Ser Gly Pro
2405                2410                2415

Phe His Tyr Trp Gly Pro Val Ile Asp Gly His Phe Leu Arg Glu
2420                2425                2430

Pro Pro Ala Arg Ala Leu Lys Arg Ser Leu Trp Val Glu Val Asp
2435                2440                2445
```

-continued

```
Leu Leu Ile Gly Ser Ser Gln Asp Asp Gly Leu Ile Asn Arg Ala
    2450                2455                2460

Lys Ala Val Lys Gln Phe Glu Ser Arg Gly Arg Thr Ser Ser
    2465                2470                2475

Lys Thr Ala Phe Tyr Gln Leu Gln Asn Ser Leu Gly Gly Glu
    2480                2485                2490

Asp Ser Asp Ala Arg Val Glu Ala Ala Thr Trp Tyr Tyr Ser
    2495                2500                2505

Leu Glu His Ser Thr Asp Asp Tyr Ala Ser Phe Ser Arg Ala Leu
    2510                2515                2520

Glu Asn Ala Thr Arg Asp Tyr Phe Ile Ile Cys Pro Ile Ile Asp
    2525                2530                2535

Met Ala Ser Ala Trp Ala Lys Arg Ala Arg Gly Asn Val Phe Met
    2540                2545                2550

Tyr His Ala Pro Glu Asn Tyr Gly His Gly Ser Leu Glu Leu Leu
    2555                2560                2565

Ala Asp Val Gln Phe Ala Leu Gly Leu Pro Phe Tyr Pro Ala Tyr
    2570                2575                2580

Glu Gly Gln Phe Ser Leu Glu Lys Ser Leu Ser Leu Lys Ile
    2585                2590                2595

Met Gln Tyr Phe Ser His Phe Ile Arg Ser Gly Asn Pro Asn Tyr
    2600                2605                2610

Pro Tyr Glu Phe Ser Arg Lys Val Pro Thr Phe Ala Thr Pro Trp
    2615                2620                2625

Pro Asp Phe Val Pro Arg Ala Gly Gly Glu Asn Tyr Lys Glu Phe
    2630                2635                2640

Ser Glu Leu Leu Pro Asn Arg Gln Gly Leu Lys Lys Ala Asp Cys
    2645                2650                2655

Ser Phe Trp Ser Lys Tyr Ile Ser Ser Leu Lys Thr Ser Ala Asp
    2660                2665                2670

Gly Ala Lys Gly Gly Gln Ser Ala Glu Ser Glu Glu Leu
    2675                2680                2685

Thr Ala Gly Ser Gly Leu Arg Glu Asp Leu Leu Ser Leu Gln Glu
    2690                2695                2700

Pro Gly Ser Lys Thr Tyr Ser Lys
    2705                2710

<210> SEQ ID NO 3
<211> LENGTH: 1574
<212> TYPE: PRT
<213> ORGANISM: Homo sapiens

<400> SEQUENCE: 3

Ile Pro Arg Lys Pro Ile Ser Lys Arg Pro Val Arg Pro Ser Leu Pro
1               5                   10                  15

Arg Ser Pro Arg Cys Pro Leu Pro Phe Asn Ala Ser Glu Val Val Gly
                20                  25                  30

Gly Thr Ile Leu Cys Glu Thr Ile Ser Gly Pro Thr Gly Ser Ala Met
            35                  40                  45

Gln Gln Cys Gln Leu Leu Cys Arg Gln Gly Ser Trp Ser Val Phe Pro
        50                  55                  60

Pro Gly Pro Leu Ile Cys Ser Leu Glu Ser Gly Arg Trp Glu Ser Gln
65                  70                  75                  80

Leu Pro Gln Pro Arg Ala Cys Gln Arg Pro Gln Leu Trp Gln Thr Ile
                85                  90                  95
```

-continued

```
Gln Thr Gln Gly His Phe Gln Leu Gln Leu Pro Pro Gly Lys Met Cys
                100                 105                 110

Ser Ala Asp Tyr Ala Gly Leu Leu Gln Thr Phe Gln Val Phe Ile Leu
            115                 120                 125

Asp Glu Leu Thr Ala Arg Gly Phe Cys Gln Ile Gln Val Lys Thr Phe
        130                 135                 140

Gly Thr Leu Val Ser Ile Pro Val Cys Asn Asn Ser Val Gln Val
145                 150                 155                 160

Gly Cys Leu Thr Arg Glu Arg Leu Gly Val Asn Val Thr Trp Lys Ser
                165                 170                 175

Arg Leu Glu Asp Ile Pro Val Ala Ser Leu Pro Asp Leu His Asp Ile
            180                 185                 190

Glu Arg Ala Leu Val Gly Lys Asp Leu Leu Gly Arg Phe Thr Asp Leu
        195                 200                 205

Ile Gln Ser Gly Ser Phe Gln Leu His Leu Asp Ser Lys Thr Phe Pro
    210                 215                 220

Ala Glu Thr Ile Arg Phe Leu Gln Gly Asp His Phe Gly Thr Ser Pro
225                 230                 235                 240

Arg Thr Trp Phe Gly Cys Ser Glu Gly Phe Tyr Gln Val Leu Thr Ser
                245                 250                 255

Glu Ala Ser Gln Asp Gly Leu Gly Cys Val Lys Cys Pro Glu Gly Ser
            260                 265                 270

Tyr Ser Gln Asp Glu Glu Cys Ile Pro Cys Pro Val Gly Phe Tyr Gln
        275                 280                 285

Glu Gln Ala Gly Ser Leu Ala Cys Val Pro Cys Pro Val Gly Arg Thr
    290                 295                 300

Thr Ile Ser Ala Gly Ala Phe Ser Gln Thr His Cys Val Thr Asp Cys
305                 310                 315                 320

Gln Arg Asn Glu Ala Gly Leu Gln Cys Asp Gln Asn Gly Gln Tyr Arg
                325                 330                 335

Ala Ser Gln Lys Asp Arg Gly Ser Gly Lys Ala Phe Cys Val Asp Gly
            340                 345                 350

Glu Gly Arg Arg Leu Pro Trp Trp Glu Thr Glu Ala Pro Leu Glu Asp
        355                 360                 365

Ser Gln Cys Leu Met Met Gln Lys Phe Glu Lys Val Pro Glu Ser Lys
    370                 375                 380

Val Ile Phe Asp Ala Asn Ala Pro Val Ala Val Arg Ser Lys Val Pro
385                 390                 395                 400

Asp Ser Glu Phe Pro Val Met Gln Cys Leu Thr Asp Cys Thr Glu Asp
                405                 410                 415

Glu Ala Cys Ser Phe Phe Thr Val Ser Thr Thr Glu Pro Glu Ile Ser
            420                 425                 430

Cys Asp Phe Tyr Ala Trp Thr Ser Asp Asn Val Ala Cys Met Thr Ser
        435                 440                 445

Asp Gln Lys Arg Asp Ala Leu Gly Asn Ser Lys Ala Thr Ser Phe Gly
    450                 455                 460

Ser Leu Arg Cys Gln Val Lys Val Arg Ser His Gly Gln Asp Ser Pro
465                 470                 475                 480

Ala Val Tyr Leu Lys Lys Gly Gln Gly Ser Thr Thr Thr Leu Gln Lys
                485                 490                 495

Arg Phe Glu Pro Thr Gly Phe Gln Asn Met Leu Ser Gly Leu Tyr Asn
            500                 505                 510

Pro Ile Val Phe Ser Ala Ser Gly Ala Asn Leu Thr Asp Ala His Leu
        515                 520                 525
```

```
Phe Cys Leu Leu Ala Cys Asp Arg Asp Leu Cys Cys Asp Gly Phe Val
    530                 535                 540
Leu Thr Gln Val Gln Gly Gly Ala Ile Ile Cys Gly Leu Leu Ser Ser
545                 550                 555                 560
Pro Ser Val Leu Leu Cys Asn Val Lys Asp Trp Met Asp Pro Ser Glu
            565                 570                 575
Ala Trp Ala Asn Ala Thr Cys Pro Gly Val Thr Tyr Asp Gln Glu Ser
            580                 585                 590
His Gln Val Ile Leu Arg Leu Gly Asp Gln Glu Phe Ile Lys Ser Leu
            595                 600                 605
Thr Pro Leu Glu Gly Thr Gln Asp Thr Phe Thr Asn Phe Gln Gln Val
            610                 615                 620
Tyr Leu Trp Lys Asp Ser Asp Met Gly Ser Arg Pro Glu Ser Met Gly
625                 630                 635                 640
Cys Arg Lys Asn Thr Val Pro Arg Pro Ala Ser Pro Thr Glu Ala Gly
                645                 650                 655
Leu Thr Thr Glu Leu Phe Ser Pro Val Asp Leu Asn Gln Val Ile Val
            660                 665                 670
Asn Gly Asn Gln Ser Leu Ser Ser Gln Lys His Trp Leu Phe Lys His
            675                 680                 685
Leu Phe Ser Ala Gln Gln Ala Asn Leu Trp Cys Leu Ser Arg Cys Val
690                 695                 700
Gln Glu His Ser Phe Cys Gln Leu Ala Glu Ile Thr Glu Ser Ala Ser
705                 710                 715                 720
Leu Tyr Phe Thr Cys Thr Leu Tyr Pro Glu Ala Gln Val Cys Asp Asp
                725                 730                 735
Ile Met Glu Ser Asn Ala Gln Gly Cys Arg Leu Ile Leu Pro Gln Met
                740                 745                 750
Pro Lys Ala Leu Phe Arg Lys Lys Val Ile Leu Glu Asp Lys Val Lys
            755                 760                 765
Asn Phe Tyr Thr Arg Leu Pro Phe Gln Lys Leu Thr Gly Ile Ser Ile
            770                 775                 780
Arg Asn Lys Val Pro Met Ser Glu Lys Ser Ile Ser Asn Gly Phe Phe
785                 790                 795                 800
Glu Cys Glu Arg Arg Cys Asp Ala Asp Pro Cys Cys Thr Gly Phe Gly
                805                 810                 815
Phe Leu Asn Val Ser Gln Leu Lys Gly Gly Glu Val Thr Cys Leu Thr
            820                 825                 830
Leu Asn Ser Leu Gly Ile Gln Met Cys Ser Glu Glu Asn Gly Gly Ala
            835                 840                 845
Trp Arg Ile Leu Asp Cys Gly Ser Pro Asp Ile Glu Val His Thr Tyr
850                 855                 860
Pro Phe Gly Trp Tyr Gln Lys Pro Ile Ala Gln Asn Asn Ala Pro Ser
865                 870                 875                 880
Phe Cys Pro Leu Val Val Leu Pro Ser Leu Thr Glu Lys Val Ser Leu
            885                 890                 895
Asp Ser Trp Gln Ser Leu Ala Leu Ser Ser Val Val Asp Pro Ser
            900                 905                 910
Ile Arg His Phe Asp Val Ala His Val Ser Thr Ala Thr Ser Asn
            915                 920                 925
Phe Ser Ala Val Arg Asp Leu Cys Leu Ser Glu Cys Ser Gln His Glu
930                 935                 940
Ala Cys Leu Ile Thr Thr Leu Gln Thr Gln Pro Gly Ala Val Arg Cys
```

```
                945            950           955           960
         Met Phe Tyr Ala Asp Thr Gln Ser Cys Thr His Ser Leu Gln Gly Gln
                        965           970           975
         Asn Cys Arg Leu Leu Leu Arg Glu Glu Ala Thr His Ile Tyr Arg Lys
                        980           985           990
         Pro Gly Ile Ser Leu Leu Ser Tyr Glu Ala Ser Val Pro Ser Val Pro
                        995           1000          1005
         Ile Ser Thr His Gly Arg Leu Leu Gly Arg Ser Gln Ala Ile Gln
                   1010          1015          1020
         Val Gly Thr Ser Trp Lys Gln Val Asp Gln Phe Leu Gly Val Pro
                   1025          1030          1035
         Tyr Ala Ala Pro Pro Leu Ala Glu Arg Arg Phe Gln Ala Pro Glu
                   1040          1045          1050
         Pro Leu Asn Trp Thr Gly Ser Trp Asp Ala Ser Lys Pro Arg Ala
                   1055          1060          1065
         Ser Cys Trp Gln Pro Gly Thr Arg Thr Ser Thr Ser Pro Gly Val
                   1070          1075          1080
         Ser Glu Asp Cys Leu Tyr Leu Asn Val Phe Ile Pro Gln Asn Val
                   1085          1090          1095
         Ala Pro Asn Ala Ser Val Leu Val Phe Phe His Asn Thr Met Asp
                   1100          1105          1110
         Arg Glu Glu Ser Glu Gly Trp Pro Ala Ile Asp Gly Ser Phe Leu
                   1115          1120          1125
         Ala Ala Val Gly Asn Leu Ile Val Val Thr Ala Ser Tyr Arg Val
                   1130          1135          1140
         Gly Val Phe Gly Phe Leu Ser Gly Ser Gly Glu Val Ser Gly
                   1145          1150          1155
         Asn Trp Gly Leu Leu Asp Gln Val Ala Ala Leu Thr Trp Val Gln
                   1160          1165          1170
         Thr His Ile Arg Gly Phe Gly Gly Asp Pro Arg Arg Val Ser Leu
                   1175          1180          1185
         Ala Ala Asp Arg Gly Gly Ala Asp Val Ala Ser Ile His Leu Leu
                   1190          1195          1200
         Thr Ala Arg Ala Thr Asn Ser Gln Leu Phe Arg Arg Ala Val Leu
                   1205          1210          1215
         Met Gly Gly Ser Ala Leu Ser Pro Ala Ala Val Ile Ser His Glu
                   1220          1225          1230
         Arg Ala Gln Gln Gln Ala Ile Ala Leu Ala Lys Glu Val Ser Cys
                   1235          1240          1245
         Pro Met Ser Ser Ser Gln Glu Val Val Ser Cys Leu Arg Gln Lys
                   1250          1255          1260
         Pro Ala Asn Val Leu Asn Asp Ala Gln Thr Lys Leu Leu Ala Val
                   1265          1270          1275
         Ser Gly Pro Phe His Tyr Trp Gly Pro Val Ile Asp Gly His Phe
                   1280          1285          1290
         Leu Arg Glu Pro Pro Ala Arg Ala Leu Lys Arg Ser Leu Trp Val
                   1295          1300          1305
         Glu Val Asp Leu Leu Ile Gly Ser Ser Gln Asp Asp Gly Leu Ile
                   1310          1315          1320
         Asn Arg Ala Lys Ala Val Lys Gln Phe Glu Glu Ser Gln Gly Arg
                   1325          1330          1335
         Thr Ser Ser Lys Thr Ala Phe Tyr Gln Ala Leu Gln Asn Ser Leu
                   1340          1345          1350
```

```
Gly Gly Glu Asp Ser Asp Ala Arg Val Glu Ala Ala Ala Thr Trp
    1355            1360            1365

Tyr Tyr Ser Leu Glu His Ser Thr Asp Asp Tyr Ala Ser Phe Ser
    1370            1375            1380

Arg Ala Leu Glu Asn Ala Thr Arg Asp Tyr Phe Ile Ile Cys Pro
    1385            1390            1395

Ile Ile Asp Met Ala Ser Ala Trp Ala Lys Arg Ala Arg Gly Asn
    1400            1405            1410

Val Phe Met Tyr His Ala Pro Glu Asn Tyr Gly His Gly Ser Leu
    1415            1420            1425

Glu Leu Leu Ala Asp Val Gln Phe Ala Leu Gly Leu Pro Phe Tyr
    1430            1435            1440

Pro Ala Tyr Glu Gly Gln Phe Ser Leu Glu Glu Lys Ser Leu Ser
    1445            1450            1455

Leu Lys Ile Met Gln Tyr Phe Ser His Phe Ile Arg Ser Gly Asn
    1460            1465            1470

Pro Asn Tyr Pro Tyr Glu Phe Ser Arg Lys Val Pro Thr Phe Ala
    1475            1480            1485

Thr Pro Trp Pro Asp Phe Val Pro Arg Ala Gly Gly Glu Asn Tyr
    1490            1495            1500

Lys Glu Phe Ser Glu Leu Leu Pro Asn Arg Gln Gly Leu Lys Lys
    1505            1510            1515

Ala Asp Cys Ser Phe Trp Ser Lys Tyr Ile Ser Ser Leu Lys Thr
    1520            1525            1530

Ser Ala Asp Gly Ala Lys Gly Gly Gln Ser Ala Glu Ser Glu Glu
    1535            1540            1545

Glu Glu Leu Thr Ala Gly Ser Gly Leu Arg Glu Asp Leu Leu Ser
    1550            1555            1560

Leu Gln Glu Pro Gly Ser Lys Thr Tyr Ser Lys
    1565            1570

<210> SEQ ID NO 4
<211> LENGTH: 12
<212> TYPE: PRT
<213> ORGANISM: Homo sapiens

<400> SEQUENCE: 4

Val Ile Phe Asp Ala Asn Ala Pro Val Ala Val Arg
1               5                   10
```